United States Patent
Libarnes et al.

(10) Patent No.: US 11,969,189 B2
(45) Date of Patent: Apr. 30, 2024

(54) MEDICAL DEVICE RELEASE SYSTEM

(71) Applicant: BOSTON SCIENTIFIC SCIMED, INC., Maple Grove, MN (US)

(72) Inventors: Ramon Libarnes, Plymouth, MN (US); Timothy A. Ostroot, Cokato, MN (US); Nicholas Lee Tassoni, Andover, MN (US); Eric Douglas Nygaard, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 451 days.

(21) Appl. No.: 17/117,367

(22) Filed: Dec. 10, 2020

(65) Prior Publication Data

US 2021/0220013 A1     Jul. 22, 2021

Related U.S. Application Data

(60) Provisional application No. 62/962,294, filed on Jan. 17, 2020.

(51) Int. Cl.
*A61B 17/12* (2006.01)
*A61B 17/34* (2006.01)
(Continued)

(52) U.S. Cl.
CPC ........... *A61B 17/3468* (2013.01); *A61B 2017/12054* (2013.01); *A61F 2/2427* (2013.01); *A61F 2002/9511* (2013.01)

(58) Field of Classification Search
CPC .......... A61B 17/12113; A61B 17/3468; A61B 2017/1205–2017/12095;
(Continued)

(56) References Cited

U.S. PATENT DOCUMENTS 6,039,744 A * 3/2000 Forber ............... A61F 2/95
                                                   606/108
6,773,448 B2 * 8/2004 Kusleika ............ A61F 2/013
                                                   606/200
(Continued)

FOREIGN PATENT DOCUMENTS

EP     1621149 A1    2/2006
EP     1728478 A1    12/2006
(Continued)

OTHER PUBLICATIONS

International Search Report and Written Opinion dated Nov. 10, 2020 for International Application No. PCT/US2020/051968.
(Continued)

*Primary Examiner* — Kathleen S Holwerda
(74) *Attorney, Agent, or Firm* — Seager, Tufte & Wickhem LLP

(57) ABSTRACT

A medical device system may include an elongate shaft having a lumen extending from a proximal end to a distal end, a proximal release wire, and a distal release wire. The proximal release wire may extend distally from a proximal end configured to remain outside the body to a distal end and may be slidably disposed within the lumen of the elongate shaft. The proximal release wire may include a distal stopper coupled to the distal end thereof. The distal release wire may extend distally from a proximal end to a distal end and may be slidably disposed within the lumen of the elongate shaft. The proximal end of the distal release wire may be slidably coupled to the distal end of the proximal release wire. The distal release wire may be configured to releasably attach a medical device to the distal end of the elongate shaft.

7 Claims, 13 Drawing Sheets

(51) Int. Cl.
*A61F 2/95* (2013.01)
*A61F 2/24* (2006.01)

(58) Field of Classification Search
CPC ....... A61F 2002/9511; A61F 2/95–2/97; A61F 2/2427
See application file for complete search history.

(56) References Cited

U.S. PATENT DOCUMENTS

| | | | | |
|---|---|---|---|---|
| 7,727,242 | B2* | 6/2010 | Sepetka | A61B 17/22031 |
| | | | | 606/127 |
| 8,083,762 | B2* | 12/2011 | Kusleika | A61M 25/09 |
| | | | | 606/200 |
| 8,777,978 | B2* | 7/2014 | Strauss | A61F 2/01 |
| | | | | 606/200 |
| 9,468,514 | B2* | 10/2016 | Berrada | A61F 2/0105 |
| 9,775,701 | B2* | 10/2017 | Kusleika | A61F 2/013 |
| 10,555,799 | B2* | 2/2020 | Kusleika | A61F 2/013 |
| 11,602,448 | B2 | 3/2023 | Nygaard | A61B 17/12022 |
| 2003/0176884 | A1* | 9/2003 | Berrada | A61F 2/0105 |
| | | | | 606/200 |
| 2006/0224180 | A1* | 10/2006 | Anderson | A61B 17/12172 |
| | | | | 606/200 |
| 2012/0071916 | A1* | 3/2012 | Kusleika | A61M 25/09 |
| | | | | 606/200 |
| 2014/0277084 | A1* | 9/2014 | Mirigian | A61B 17/0467 |
| | | | | 606/200 |
| 2016/0038150 | A1* | 2/2016 | Lorenzo | A61B 17/12154 |
| | | | | 606/200 |
| 2016/0106449 | A1* | 4/2016 | Brady | A61F 2/013 |
| | | | | 606/159 |
| 2017/0112512 | A1* | 4/2017 | Davidson | A61B 17/22031 |
| 2018/0228493 | A1* | 8/2018 | Aguilar | A61B 17/1214 |
| 2019/0105055 | A1 | 4/2019 | Cao et al. | |
| 2019/0254678 | A1 | 8/2019 | Dinges et al. | |
| 2020/0229957 | A1* | 7/2020 | Bardsley | A61F 2/966 |

FOREIGN PATENT DOCUMENTS

| | | |
|---|---|---|
| EP | 1441649 B1 | 8/2011 |
| JP | 2018534995 A | 11/2018 |
| WO | 2003075997 A1 | 9/2003 |
| WO | 2017075358 A2 | 5/2017 |

OTHER PUBLICATIONS

International Search Report and Written Opinion dated Mar. 16, 2021 for International Application No. PCT/US2020/064240.

* cited by examiner

MEDICAL DEVICE RELEASE SYSTEM

CROSS-REFERENCE TO RELATED APPLICATIONS

This application claims the benefit of priority of U.S. Provisional Application No. 62/962,294 filed Jan. 17, 2020, the entire disclosure of which is hereby incorporated by reference.

TECHNICAL FIELD

The present disclosure pertains to medical devices and methods for manufacturing and/or using medical devices. More particularly, the present disclosure pertains to configurations of a system for releasing medical implants.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first example, a medical device system may comprise an elongate shaft having a lumen extending from a proximal end of the elongate shaft to a distal end of the elongate shaft, a proximal release wire extending distally from a proximal end configured to remain outside a body to a distal end and slidably disposed within the lumen of the elongate shaft, a distal stopper coupled to the distal end of the proximal release wire, and a distal release wire extending distally from a proximal end to a distal end and slidably disposed within the lumen of the elongate shaft. The proximal end of the distal release wire may be slidably coupled to the distal end of the proximal release wire proximal to the distal stopper. The distal release wire may be configured to releasably attach a medical device to the distal end of the elongate shaft.

Alternatively or additionally to any of the examples above, in another example, the medical device system may further comprise a proximal stopper coupled to the proximal release wire proximal to the distal stopper.

Alternatively or additionally to any of the examples above, in another example, the proximal end of the distal release wire may be disposed between the proximal stopper and the distal stopper.

Alternatively or additionally to any of the examples above, in another example, the proximal stopper may have an outer diameter that is greater than an outer diameter of the proximal release wire.

Alternatively or additionally to any of the examples above, in another example, the distal stopper may have an outer diameter that is greater than an outer diameter of the proximal release wire.

Alternatively or additionally to any of the examples above, in another example, the proximal end of the distal release wire may be formed into a helical coil disposed about the proximal release wire.

Alternatively or additionally to any of the examples above, in another example, the distal stopper may have an outer diameter that is greater than an inner diameter of the helical coil.

Alternatively or additionally to any of the examples above, in another example, the distal stopper may be a loop formed from a distal end of the proximal release wire.

Alternatively or additionally to any of the examples above, in another example, the distal stopper may comprise a generally cylindrical collar defining a lumen extending therethrough, the distal release wire slidably disposed within the lumen of the generally cylindrical collar.

Alternatively or additionally to any of the examples above, in another example, the proximal end of the distal release wire may be formed into a loop.

Alternatively or additionally to any of the examples above, in another example, the proximal end of the distal release wire may be a three-dimensional shape having an outer dimension greater than a diameter of a lumen of the loop.

Alternatively or additionally to any of the examples above, in another example, the proximal end of the distal release wire may comprise a generally cylindrical collar defining a lumen extending therethrough. The proximal release wire may be slidably disposed within the lumen of the generally cylindrical collar of the distal release wire.

Alternatively or additionally to any of the examples above, in another example, the distal stopper may be configured to physically engage with the proximal end of the distal release wire.

Alternatively or additionally to any of the examples above, in another example, the proximal release wire may be configured to move proximally along a longitudinal axis of the elongate shaft independently from the distal release wire over a predetermined axial distance.

Alternatively or additionally to any of the examples above, in another example, proximal movement of the proximal release wire may be greater than the predetermined axial distance is configured to move the distal release wire in concert with the proximal release wire.

In another example, a medical device system may comprise an elongate shaft having a lumen extending from a proximal end of the elongate shaft to a distal end of the elongate shaft, a proximal release wire extending distally from a proximal end configured to remain outside a body to a distal end including a distal stopper, the distal stopper having a greater cross-sectional dimension than an intermediate region of the proximal release wire and slidably disposed within the lumen of the elongate shaft, and a distal release wire extending distally from a proximal end including a helical coil to a generally linear distal end and slidably disposed within the lumen of the elongate shaft, the helical coil of the distal release wire slidably disposed over the intermediate region of the proximal release wire. The distal release wire may be configured to releasably attach a medical device to the distal end of the elongate shaft. Proximal movement of the proximal release wire over a first distance may move the proximal release wire independent of the distal release wire and proximal movement of the proximal release wire over a second distance greater than the first distance may be configured to move the distal release wire in concert with the proximal release wire.

Alternatively or additionally to any of the examples above, in another example, the first distance may be equal to or less than a distance between a proximal end of the distal stopper and a distal end region of the helical coil.

Alternatively or additionally to any of the examples above, in another example, the proximal end of the distal stopper may be configured to engage an inner surface or a distal end of the helical coil of the distal release wire upon proximal actuation of the proximal release wire a distance greater than the first distance.

Alternatively or additionally to any of the examples above, in another example, at least a portion of the distal release wire may extend generally parallel to the intermediate region of the proximal release wire.

In another example, a medical device system may comprise an elongate shaft having a lumen extending from a proximal end of the elongate shaft to a distal end of the elongate shaft, a proximal release wire extending distally from a proximal end configured to remain outside a body to a distal end and slidably disposed within the lumen of the elongate shaft, a distal stopper coupled to the distal end of the proximal release wire, a proximal stopper coupled to the proximal release wire proximal to the distal stopper, and a distal release wire extending distally from a proximal end to a generally linear distal end and slidably disposed within the lumen of the elongate shaft, the proximal end of the distal release wire comprising a plurality of windings slidably coupled over a linear portion of the proximal release wire. The distal release wire may be configured to releasably attach a medical device to the distal end of the elongate shaft. Proximal movement of the proximal release wire over a first distance may moves the proximal release wire independent of the distal release wire and proximal movement of the proximal release wire over a second distance greater than the first distance may be configured to move the distal release wire in concert with the proximal release wire.

Alternatively or additionally to any of the examples above, in another example, the proximal end of the distal release wire may be slidably disposed between the proximal stopper and the distal stopper.

Alternatively or additionally to any of the examples above, in another example, the distal stopper may have an outer diameter greater than an inner diameter of the plurality of windings.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
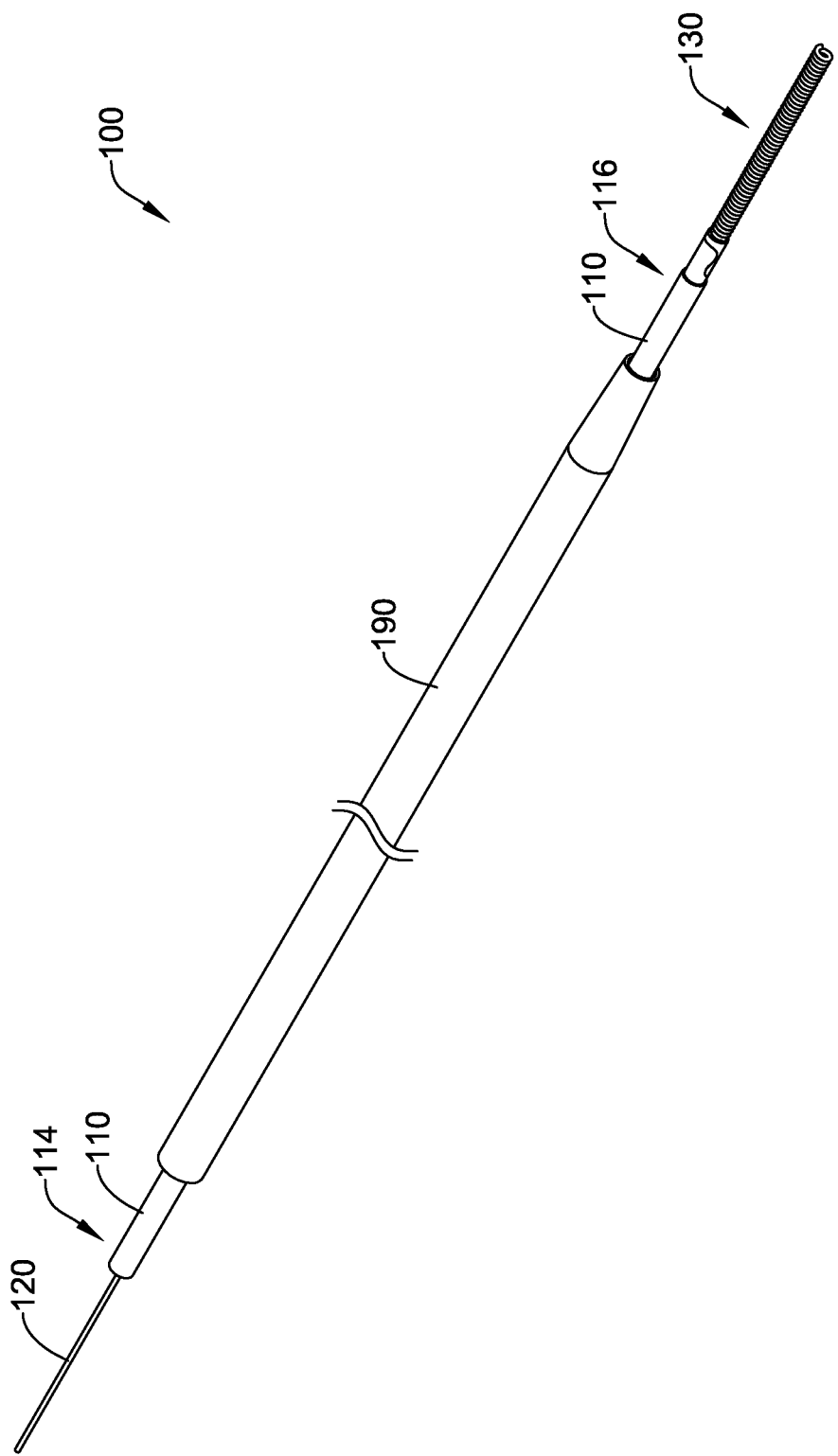
FIG. 1 is a perspective view of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean a greatest measurement of a stated or identified dimension, unless specifically referred to as a minimum extent. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. However, where referred to as a "minimum extent", the "extent" shall refer to a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact and/or are affected by the cardiovascular system are prevalent throughout the world. For example, some forms of arterial venous malformations (AVMs) may "feed" off of normal blood flow through the vascular system. Without being bound by theory, it is believed that it may be possible to treat, at least partially, arterial venous malformations and/or other diseases or conditions by starving them of normal, oxygen and/or nutrient-rich blood flow, thereby limiting their ability to grow and/or spread. Other examples of diseases or conditions that may benefit from vascular occlusion include, but are not limited to, bleeds, aneurysms, venous insufficiency, shutting off blood flow prior to organ resection, or preventing embolic bead reflux into branch vessels in the liver. Disclosed herein are medical devices that may be used within a portion of the cardiovascular system in order to treat and/or repair some arterial venous malformations and/or other diseases or conditions. The devices disclosed herein may also provide a number of additional desirable features and benefits as described in more detail below.

Figure 2:
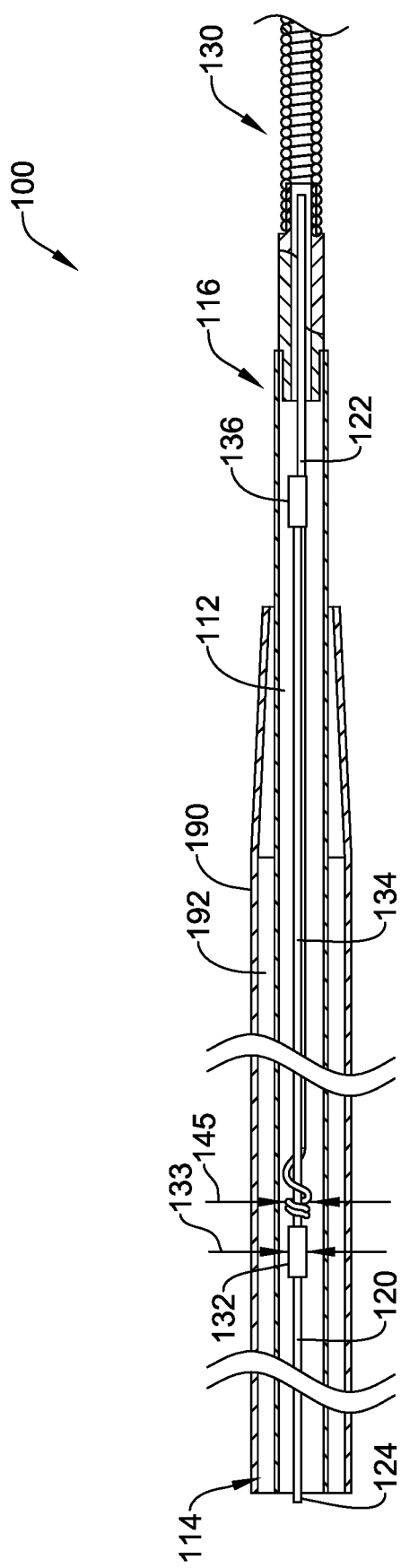
FIG. 2 is a partial cross-sectional view of the illustrative medical device system of FIG. 1.

FIGS. 1 and 2 illustrate aspects of an example medical device system 100. The medical device system 100 may include an elongate shaft 110 having a lumen 112 (e.g., FIG. 2) extending from a proximal end 114 of the elongate shaft 110 to a distal end 116 of the elongate shaft 110. In some embodiments, the elongate shaft 110 may be a catheter, a hypotube, or other similar tubular structure. In some embodiments, at least a portion of the elongate shaft 110 may include micromachining, a plurality of cuts or weakened areas, some degree of material removal, etc. to provide increased flexibility along a length of the elongate shaft 110 for navigating tortuous vasculature. Some suitable but non-limiting materials for the elongate shaft 110, for example metallic materials, polymer materials, composite materials, etc., are described below.

The medical device system 100 may include a proximal release wire (or a delivery system pull wire) 120 and a distal release wire (or a coupler pull wire) 122 (e.g., FIG. 2) slidably disposed within the lumen 112 of the elongate shaft 110. A medical device 130 may be disposed proximate the distal end 116 of the elongate shaft 110. The proximal and distal release wires 120, 122 may be axially slidable between an interlocked position and a released position relative to the medical device 130, as will be described in more detail herein. The proximal and distal release wires 120, 122 may be configured to releasably attach the medical device 130 to the distal end 116 of the elongate shaft 110. The medical device 130 may be configured to expand from a delivery configuration to a deployed configuration. For simplicity, the medical device 130 is illustrated herein as an embolic coil, but other suitable medical devices transported, delivered, used, released, etc. in a similar manner are also contemplated, including but not limited to, vascular occlusion device, stents, embolic filters, replacement heart valves, other occlusion devices, and/or other medical implants, etc.

In some embodiments, the proximal and/or distal release wires 120, 122 may be alternately and/or interchangeably referred to as a pull wire, an actuation wire, and/or a locking wire. The proximal and distal release wires 120, 122 may generally be a solid wire or shaft, but may also be tubular in some embodiments. Some suitable but non-limiting materials for the release wires 120, 122 for example, metallic materials, polymer materials, composite materials, etc., are described below.

In some embodiments, the medical device system 100 may include a microcatheter 190 sized and configured to deliver the medical device 130 to a treatment site in a delivery configuration. The elongate shaft 110 and the medical device 130 may be slidably disposed within a lumen 192 (e.g., FIG. 2) of the microcatheter 190. In some embodiments, the microcatheter 190 may facilitate percutaneous delivery of the medical device 130 to the treatment site. For reference only, the medical device 130 may be shown in the figures (e.g., FIGS. 1-9) in the delivery configuration or an at least partially-deployed configuration. The skilled person will recognize that the medical device 130 may be expanded and/or coiled upon itself when the medical device 130 is deployed. Some suitable but non-limiting materials for the microcatheter 190, for example metallic materials, polymer materials, composite materials, etc., are described below.

Figure 3:
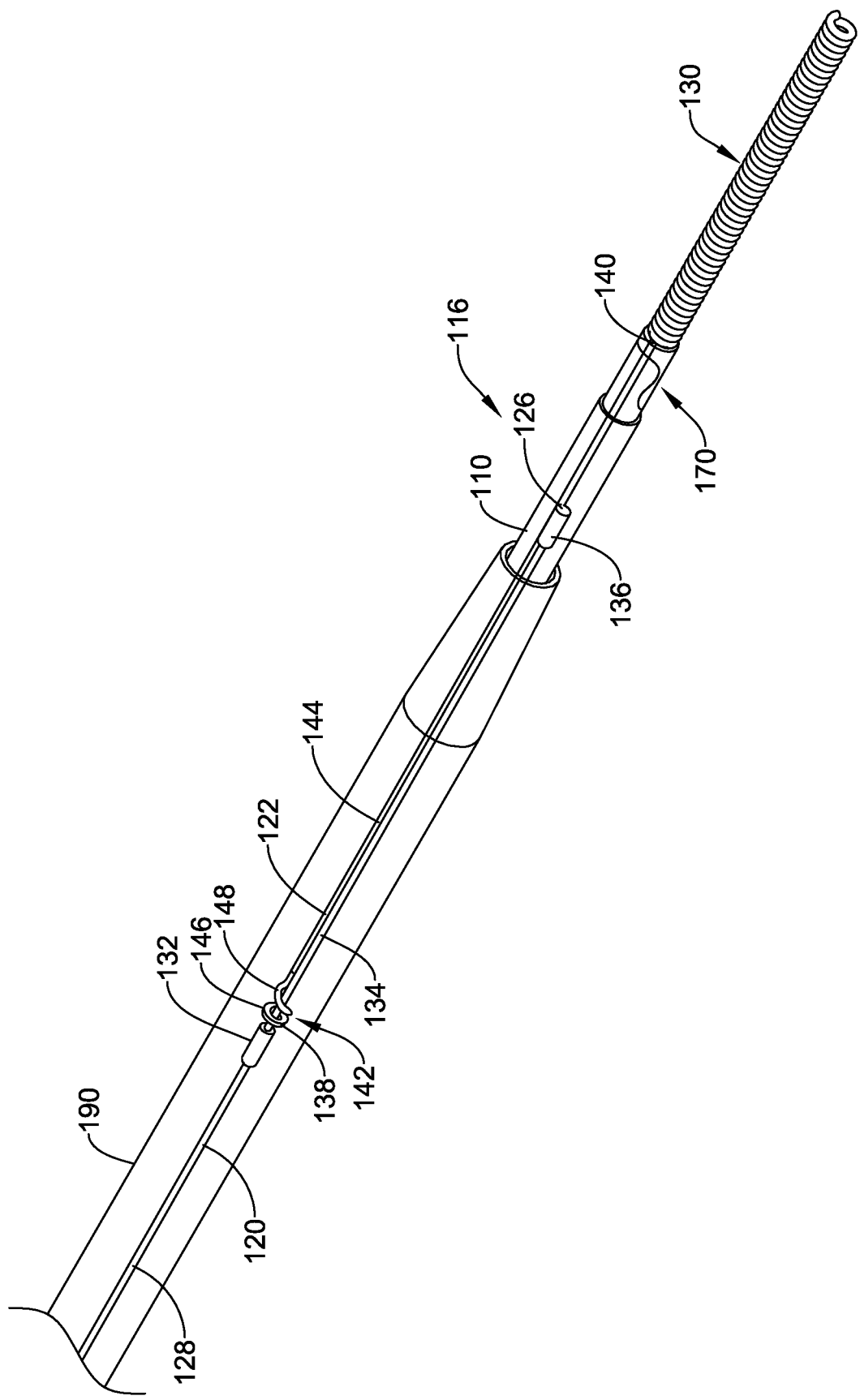
FIG. 3 is a perspective view of a distal portion of the illustrative medical device system of FIG. 1.

FIG. 3 illustrates an enlarged perspective view of the distal end 116 of the elongate shaft 110 with the elongate shaft 110, the medical device 130, and the microcatheter 190 shown in transparency. The proximal release wire 120 may be a generally elongate structure extending distally from a proximal end 124 (e.g., FIG. 2) configured to remain outside of the body to a distal end 126. The proximal end 124 of the proximal release wire 120 may be actuatable by the user to control release of the medical device 130. In some cases, the distal end 126 of the proximal release wire 120 may be positioned proximal to the medical device 130. The proximal release wire 120 may include a first region 128 extending distally from the proximal end 124 to a proximal stopper 132 and a second region 134 extending distally from the proximal stopper 132 to a distal stopper 136. A distal end of the distal stopper 136 may form the distal end 126 of the proximal release wire 120. The proximal and distal stoppers 132, 136 may be an enlarged portion of the proximal release wire 120 which may each have a diameter that is greater than a diameter of the first and/or second regions 128, 134. However, the proximal and distal stoppers 132, 136 need not have the same cross-sectional dimension. Further, while the proximal and/or distal stopper 132, 136 are illustrated as having a generally cylindrical shape, they may take any 3-dimensional shape desired, such as, but not limited to, spherical, cuboid, rectangular prism, conical, etc. Similarly, the first and/or second regions 128, 134 of the proximal release wire 120 may have a cross-sectional shape other than circular, such as, but not limited to, square, rectangular, oblong, polygonal, etc. In some cases, the proximal release wire 120 may be formed as a single monolithic structure. In other cases, the proximal release wire 120 may be formed from two or more components that have been fixedly coupled together. For example, one or both stoppers 132, 136 may be formed separately and coupled (e.g., adhered, welded, soldered, etc.) to a wire which forms the first and/or second regions 128, 134.

The distal release wire 122 may be a generally elongate structure formed from a wire or filament and extending distally from a proximal end 138 to a distal end 140. While the distal release wire 122 is illustrated as having a generally circular cross-sectional shape, the distal release wire 122 may have other cross-sectional shapes, such as, but not limited to, square, rectangular, oblong, polygonal, etc. The distal end 140 of the distal release wire 122 may be slidably coupled with a release mechanism 170 as will be described in more detail herein. The proximal end 138 may be positioned between the proximal stopper 132 and the distal stopper 136 of the proximal release wire 120 such that a length of the distal release wire 122 extends along and generally parallel to a length of the proximal release wire 120. In some cases, the proximal end 138 of the distal release wire 122 may be positioned closer to or adjacent to the proximal stopper 132 of the proximal release wire 120, for example, when the distal release wire 122 is interlocked with the release mechanism 170, although this is not required. In other cases, the proximal end 138 of the distal release wire 122 may be positioned closer to or adjacent to the distal stopper 136 of the proximal release wire 120, for example, when the distal release wire 122 is free from engagement with the release mechanism 170, although this is not required. It is contemplated that the positioning of the proximal end 138 of the distal release wire 122 may be determined at least in part by a desired slip distance, or a desired length the proximal release wire 120 and/or distal release wire 122 can stretch or move without releasing the medical device 130.

The proximal end 138 of the distal release wire 122 may be wrapped around the second region 134 of the proximal release wire to form a helical coil 142. For example, the distal release wire 122 may be helically wound about the proximal release wire 120 such that the helical coil 142 and/or the proximal release wire 120 are in an interlocked relationship and longitudinally slidable relative to one another, as will be described in more detail herein. The helical coil 142 may including any number of helical windings desired, such as, but not limited to, less than one, one, two, three, four, or more. It is further contemplated that one or more of the helical windings may form less than a complete 360° revolution. In some cases, the one or more helical windings may comprise a single winding having less than a complete 360° revolution. The helical coil 142 may include a first portion 146 having one or more windings that are tightly wound which then transition into a loose pitch winding such that the runoff wire (or a transition region) 148 from the helical coil 142 to a generally linear portion 144 is co-axial with the tightly wound portion 146. The transition region 148 may also facilitate loading the distal release wire 122 during assembly and mitigate advancement and/or retraction forces by minimizing interaction of the distal release wire 122 with the inner wall of the elongate shaft 110. In some cases, each winding of the first portion 146 need not have the same pitch. It is further contemplated that the helical coil 142 may have an outer diameter 145 (see, for example, FIG. 2) that is configured to mechanically interface or physically engage with (e.g., frictionally engage) an inner surface of the elongate shaft 110. This mechanical engagement between the distal release wire 122 and the elongate shaft 110 may help maintain the position of the distal release wire 122 relative to the release mechanism 170.

The proximal stopper 132 may have an outer diameter 133 (see, for example, FIG. 2) that is greater than an inner diameter 168 (see, for example, FIG. 6) of the helical coil 142. This may allow the proximal stopper 132 to exert a pushing force on the proximal end 138 of the distal release wire 122. The pushing force may allow the proximal release wire 120 to facilitate loading of the proximal release wire 120 and the distal release wire 122 within the elongate shaft 110 without the proximal stopper 132 and the helical coil 142 wedging together.

As described herein, the proximal end 138 of the distal release wire 122 may be disposed between the proximal stopper 132 and the distal stopper 136 of the proximal release wire 120. This may allow the proximal release wire 120 and the distal release wire 122 to be slidably coupled to one another over a limited or predetermined axial distance (e.g., along a longitudinal axis of the system 100). It is contemplated that the proximal release wire 120 and the distal release wire 122 may each move independently relative to one another over the limited axial distance. The length of second region 134 (or the distance between the proximal stopper 132 and the distal stopper 136) may determine how far the proximal release wire 120 and/or distal release wire 122 can slide independently before engaging the other component 120, 122 and moving it as well.

The sliding arrangement of the proximal release wire 120 and the distal release wire 122 may help mitigate premature detachment of the medical device 130. For example, when the delivery system 100 (and the medical device 130) is proximally retracted (and at other times during use), the elongate shaft 110 can experience tensile loading. In other words, the distal portion of the elongate shaft 110 may stretch, which could cause the retention wire to prematurely detach from the medical device 130. The proximal end 124 of the proximal release wire 120 (or a region adjacent thereto) may be coupled to the proximal end 114 of the elongate shaft 110 (or a region adjacent thereto) to limit or prevent movement of the proximal release wire 120 relative to the elongate shaft. However, this may cause the proximal release wire 120 to stretch with the elongate shaft 110. The sliding arrangement of the proximal release wire 120 and the distal release wire 122 may allow the proximal release wire 120 to move proximally (e.g., stretch) as the distal portion of the elongate shaft 110 stretches without exerting a proximal force on the distal release wire 122.

Figure 4:
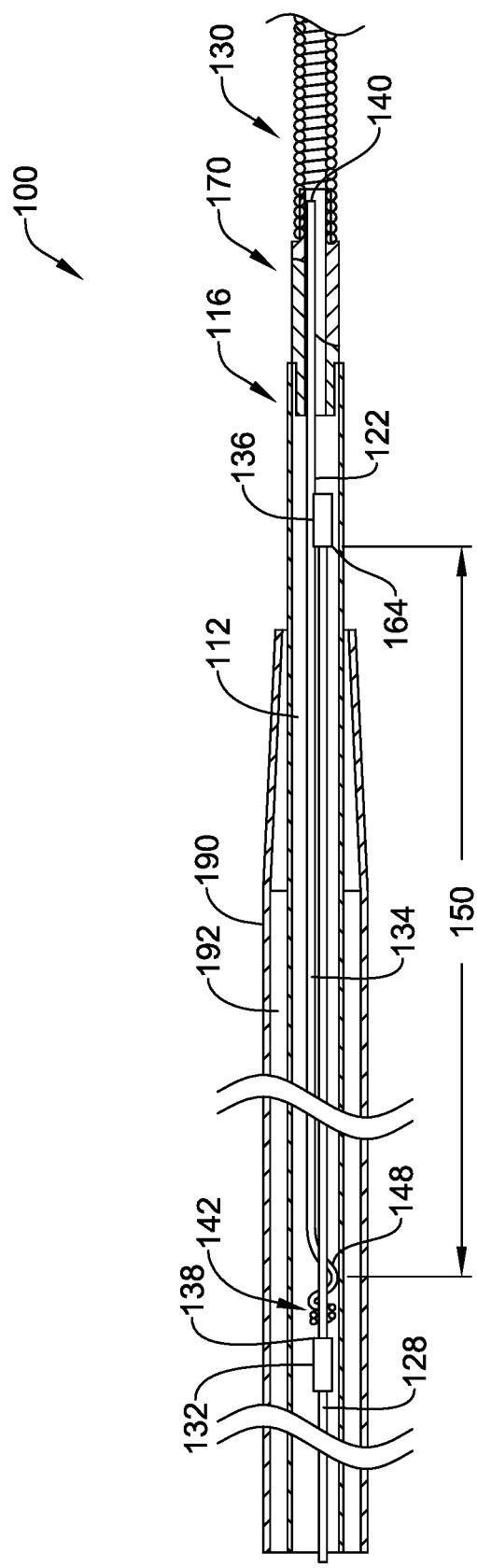
FIG. 4-8 illustrate actuation of a portion of an example medical device system.

FIGS. 4-9 generally illustrate the medical device 130 being released from the elongate shaft 110, such as at a treatment site, for example. In use, the microcatheter 190 of the medical device system 100 may be inserted into a patient's anatomy and a distal end of the microcatheter 190 may be guided and/or advanced to a location adjacent to a treatment site. The medical device 130 disposed at and/or proximate the distal end 116 of the elongate shaft 110 may be inserted into a proximal end of the lumen 192, disposed within the microcatheter 190, and advanced through and/or with the microcatheter 190 to the treatment site. In some embodiments, the medical device 130 may be disposed within the lumen 192 of the microcatheter 190 proximate the distal end of the microcatheter 190. In some embodiments, the medical device 130 may be disposed within the lumen 192 of the microcatheter 190 proximate the distal end of the microcatheter 190 prior to use and/or prior to inserting the microcatheter 190 into the patient's anatomy. Deployment and/or release of the medical device 130 may be performed selectively depending upon the type of medical device and/or the desired treatment process or method. When ready to deploy the medical device 130, the elongate shaft 110 may be advanced and/or translated distally relative to the microcatheter 190 until the medical device 130 is exposed and/or disposed distal of the microcatheter 190, as shown in FIG. 4. Alternatively, the microcatheter 190 may be withdrawn relative to the elongate shaft 110 until the medical device 130 is exposed and/or disposed distal of the microcatheter 190. For clarity, the microcatheter 190 is shown in a proximally retracted configuration. However, during navigation through the body, the microcatheter may be disposed over the medical device 130.

A release mechanism 170 may releasably attach the medical device 130 to the distal end 116 of the elongate shaft 110. In some embodiments, the elongate shaft 110 may include a first portion 172 of the release mechanism 170 fixedly attached to the distal end 116 of the elongate shaft 110 and the medical device 130 may include a second portion 174 of the release mechanism 170 fixedly attached to a proximal end of the medical device 130. A distal end 140 of the distal release wire 122 may slidably engage with the first portion 172 of the release mechanism 170 and the second portion 174 of the release mechanism 170 in the interlocked position, as seen in FIG. 4. The distal release wire 122 interlocks the first portion 172 of the release mechanism 170 with the second portion 174 of the release mechanism 170 when the proximal release wire 120 and the distal release wire 122 are in the delivery configuration, as shown in FIG. 4. It should be noted that the delivery configuration does not require the proximal stopper 132 of the proximal release wire 120 to abut or contact the proximal end 138 of the distal release wire 122 nor does the delivery configuration require the distal stopper 136 to abut or contact the first portion 172 of the release mechanism 170. In some cases, an outer diameter 166 of distal stopper 136 may be greater than an inner diameter of the release mechanism 170. This may prevent or reduce unintentional distal advancement of the proximal release wire 120 and/or the distal release wire 122 into the lumen of the medical device 130

FIG. 4 illustrates the proximal release wire 120 and distal release wire 122 in an arrangement which allows for the greatest slip joint clearance 150. The slip joint clearance 150 may dictate how much the elongate shaft 110 can stretch before motion of the distal release wire 122 is seen. The slip joint clearance 150 may be the distance between a proximal end 164 of the distal stopper 136 and a point in the helical coil 142 where the inner diameter thereof is less than an outer diameter of the distal stopper 136. The slip joint clearance 150 can be modified by changing a length of the second region 134 (or a distance between the proximal and distal stoppers 132, 136). It is contemplated that the distance between the proximal and distal stoppers 132, 136 may be adjusted to withstand essentially any stretch target. In some cases, the second region 134 of the proximal release wire 120 may have a length in the range of about 0.2 inches (0.51 centimeters (cm)) to about 0.5 inches (1.27 cm), about 0.28 inches (0.71 cm) to about 0.43 inches (1.09 cm), or about 0.34 inches (0.86 cm). It is contemplated that the second region 134 of the proximal release wire 120 may have a length of 0.2 inches (0.51 cm) or greater than 0.5 inches (1.27 cm) depending on the application.

Figure 5:
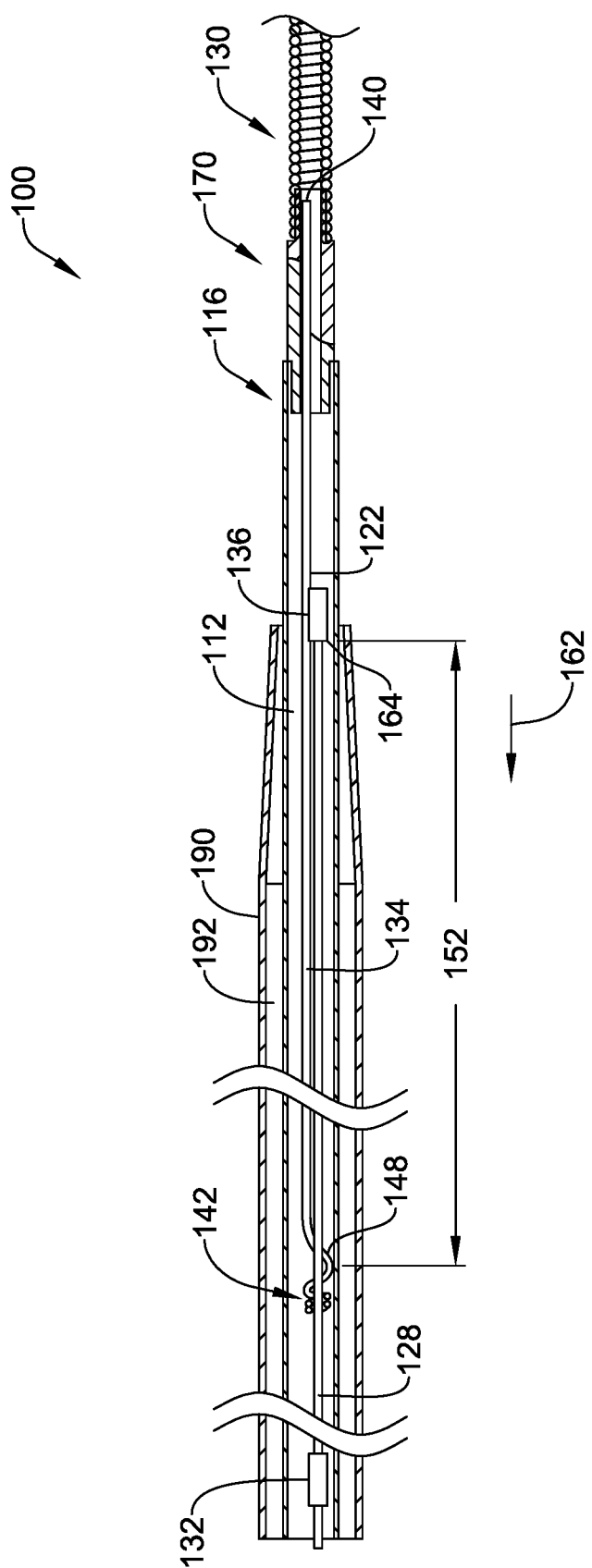

As the delivery system 100 is distally advanced to the treatment location, the elongate shaft 110 may start to stretch. In some instances, the proximal release wire 120 may be coupled to the elongate shaft 110 to prevent longitudinal movement of the proximal release wire 120 relative to the elongate shaft 110 during delivery. This may cause the proximal release wire 120 to stretch with the elongate shaft 110. FIG. 5 illustrates the proximal release wire 120 and the distal release wire 122 absorbing some of the stretch. As can be seen in FIG. 5, the proximal release wire 120 has shifted in the proximal direction, as indicated by arrow 162, while the distal release wire 122 remains longitudinally fixed. As can be seen in FIG. 5, there remains a length 152 of clearance between the distal stopper 136 and the helical coil 142. However, the length 152 is less than the length 150 of the configuration illustrated in FIG. 4. The movement of the proximal release wire 120 may be due to stretching or user actuation.

Figure 6:
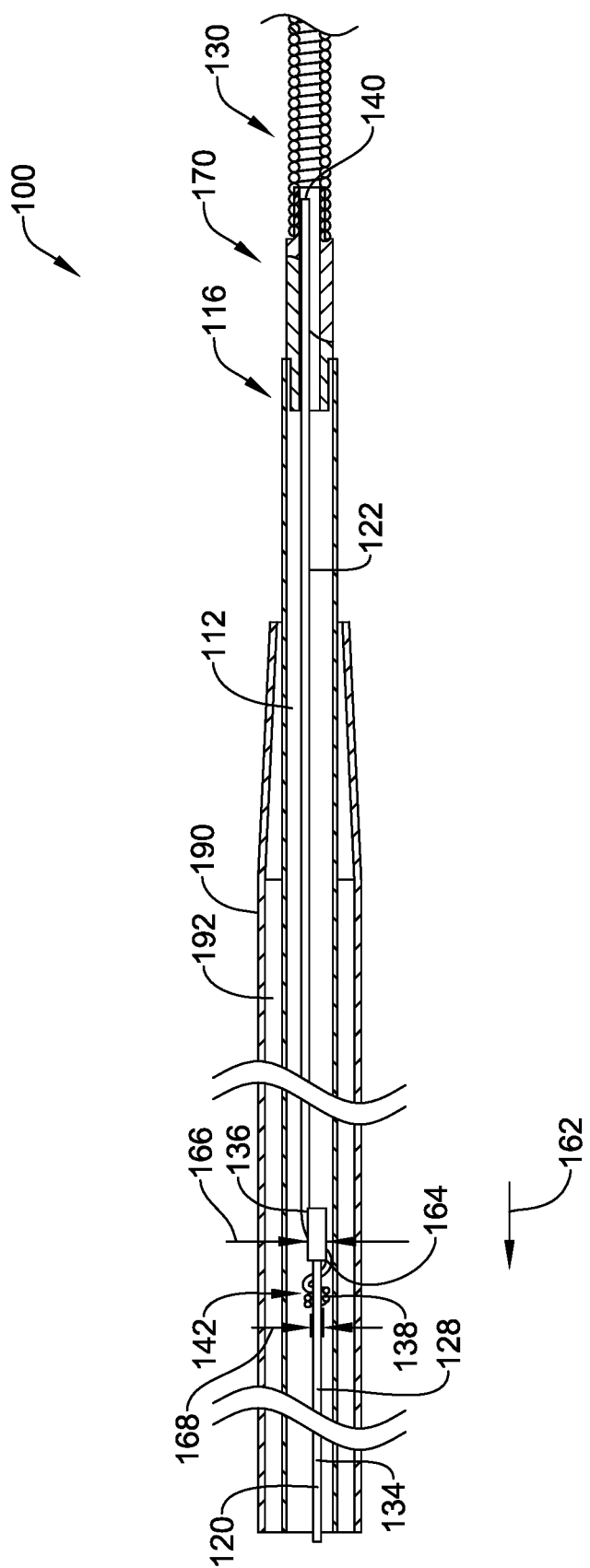
Figure 7:
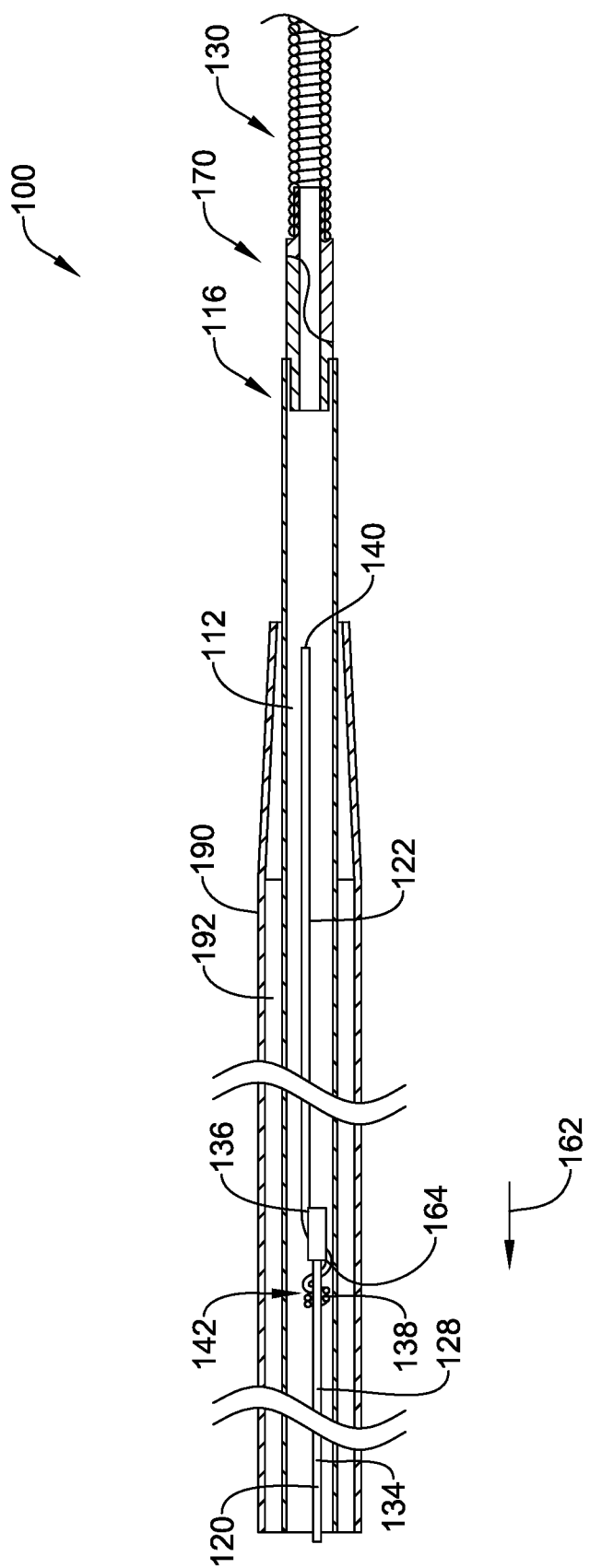

When detachment of the medical device 130 is desired, the user may uncouple the elongate shaft 110 and the proximal release wire 120, if so attached, to allow for proximal retraction of the proximal release wire 120. It is contemplated that the inner diameter 168 of the helical coil 142 may be larger than the outer diameter of the second region 134 of the proximal release wire 120. This may minimize surface contact between the proximal release wire 120 and the helical coil 142 and thus reduce friction between the proximal release wire 120 and the distal release wire 122. The proximal end 124 of the proximal release wire 120 may be proximally actuated, as shown at arrow 162, over a first distance until a length of the clearance between the distal stopper 136 and the helical coil 142 has been used up, as shown in FIG. 6. As illustrated in FIG. 6, the clearance has been used up when the proximal end 164 of the distal stopper 136 contacts the helical coil 142 in such a manner that further proximal actuation of the proximal release wire 120 will result in simultaneous proximal movement of the distal actuation wire 122. It is contemplated that the length of the distance between the distal stopper 136 and the helical coil 142 may be variable depending on the degree of stretching of the elongate shaft 110 and/or the original configuration of the proximal and distal stoppers 132, 136 and/or the helical coil 142. Once the proximal end 164 of the distal stopper 136 engages one or both of an inner surface or a distal surface of the helical coil 142 of the distal release wire 122, further proximal movement over a second distance of the proximal release wire 120 results in proximal actuation of the distal release wire 122 in concert with the proximal release wire 120, as shown in FIG. 7. In some cases, the distal stopper 136 may have an outer diameter 166 that is greater than an inner diameter 168 of the helical coil 142 to create a mechanical engagement between the distal stopper 136 and the helical coil 142. In some cases, the outer diameter 166 of the distal stopper 136 and/or the outer diameter of the proximal stopper 132 may be adjusted to perform as a stop against other features of the delivery system and/or to center the proximal release wire 120 within the lumen 112 of the elongate shaft 110.

As described herein, the helical coil 142 of the distal release wire 122 may have an interference fit with (or otherwise frictionally or physically engage) the inner wall of the elongate shaft 110. This may secure the distal release wire 122 until a force is intentionally applied by the user to the proximal release wire 120. Such an arrangement may help reduce passive migration of the distal release wire 122. Further, as described herein, the inner diameter 168 of the helical coil 142 may be greater than the diameter of the second region 134 of the proximal release wire 120 to allow the second region 134 of the proximal release wire 120 to pass therethrough with little to no friction.

Figure 8:
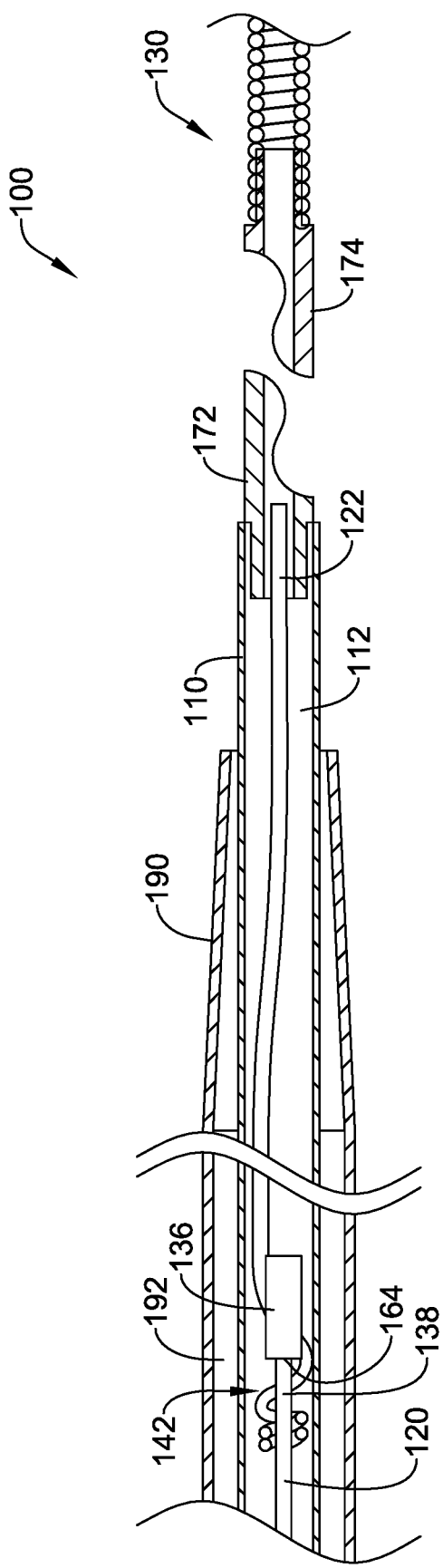
Figure 9:
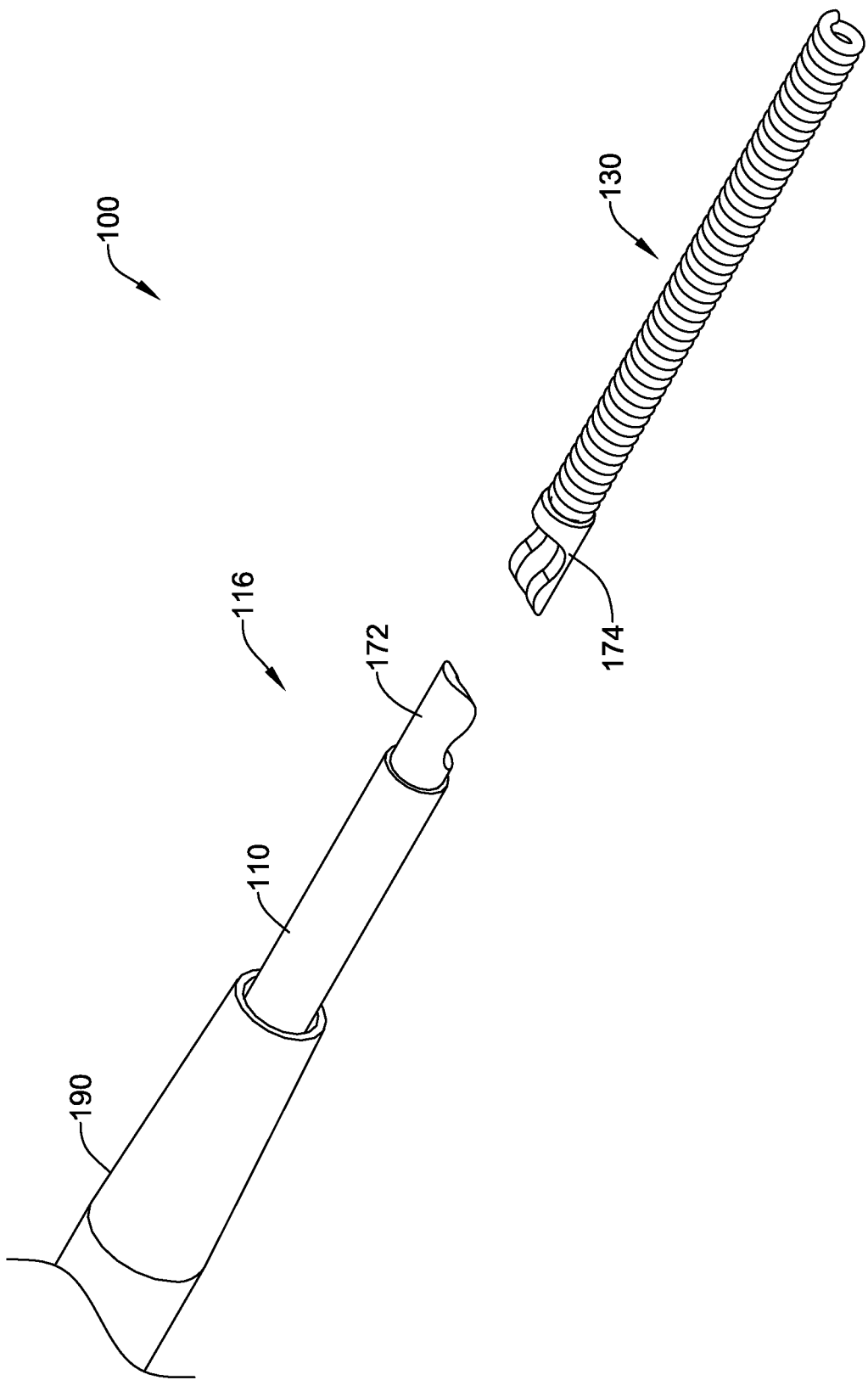
FIG. 9 illustrates an example release mechanism of an example medical device system.

It is contemplated that the release mechanism 170 may remain in an interlocked configuration until the distal release wire 122 has been proximally actuated by a length equal to or greater than the length of the release mechanism 170. FIGS. 8 and 9 illustrate the system 100 with the medical device 130 in a deployed configuration. For example, proximal actuation of the distal release wire 122 by a length less than a length of the release mechanism 170 may not be sufficient to release the medical device 130. In at least some embodiments, the distal release wire 122 may be slidably disposed within the lumen 112 extending through the elongate shaft 110, a first axial lumen extending through the first portion 172 of the release mechanism 170, and a second axial lumen extending through the second portion 174 of the release mechanism 170. It is contemplated that the release of the medical device 130 may be reversed at any axial location of the distal release wire 122 between the interlocked configuration and a fully released configuration (e.g., FIGS. 8 and 9). The first axial lumen of the first portion 172 and the second axial lumen of the second portion 174 may be substantially coaxial with the central longitudinal axis and/or the distal release wire 122 when the medical device 130 is releasably attached to the distal end 116 of the elongate shaft 110. Some suitable but non-limiting materials for the release mechanism 170, the first portion 172, and the second portion 174, for example metallic materials, polymer materials, composite materials, etc., are described below.

Referring back to FIGS. 7 and 8, while not explicitly shown, the elongate shaft 110 may have sufficient length such that the proximal end 114 of the elongate shaft 110 and/or the proximal release wire 120 remains proximal of (e.g., extends proximally from) the microcatheter 190 when the medical device 130 is disposed distal of the microcatheter 190. In use, the elongate shaft 110 may have sufficient length to reach from the treatment site to a position outside of the patient where the medical device system 100 may be manipulated by an operator (e.g., clinician, physician, user, etc.). After insertion of the medical device system 100 to the treatment site, the operator of the medical device system 100 may place a first hand on the proximal end 114 of the elongate shaft 110 and a second hand on the proximal end 124 of the proximal release wire 120 in order to manipulate the proximal release wire 120 and/or the distal release wire 122 to release the medical device 130

While not explicitly shown, the medical device system 100 may include an introducer configured to load the medical device 130 into the microcatheter 190. The introducer may be a tubular member having a lumen extending from a proximal end to a distal end. The introducer may hold the medical device 130 to a reduced diameter and/or in a delivery configuration for loading into the microcatheter 190. After loading the medical device 130 into the microcatheter 190, the introducer may be proximally withdrawn over and relative to the elongate shaft 110 and removed from the medical device system 100.

In use, a method of delivering the medical device 130 to a treatment site (e.g., a vein, an artery, etc.) may include inserting the microcatheter 190 into a patient's anatomy and guiding the distal end of the microcatheter 190 to a location adjacent the treatment site. The method may include inserting the medical device 130 disposed at and/or proximate the distal end 116 of the elongate shaft 110 into a proximal end of the lumen 192 disposed within the microcatheter 190. In some embodiments, the medical device 130 may be inserted into the lumen 192 of the microcatheter 190 after the microcatheter 190 is inserted into the patient's anatomy. The method may include advancing the medical device 130 through the microcatheter 190 to the treatment site. The medical device 130 may be releasably attached to the distal end 116 of the elongate shaft 110 by a pull wire (e.g., proximal release wire 120 and/or distal release wire 122, etc.) extending through the lumen 112 within the elongate shaft 110. The proximal release wire 120 may extend proximally from the elongate shaft 110, and the proximal release wire 120 may be releasably coupled to the elongate shaft 110. Alternatively, in some embodiments, the medical device 130 may be inserted into the proximal end of the lumen 192 of the microcatheter 190 and advanced through the microcatheter 190 to a distal end of the microcatheter 190 before the microcatheter 190 is inserted into the patient's anatomy.

As discussed herein, the first portion 172 of the release mechanism 170 may be attached to the distal end 116 of the elongate shaft 110, and the second portion 174 of the release mechanism 170 may be fixedly attached to a proximal end of the medical device 130. The proximal release wire 120 and/or distal release wire 122 may be slidably disposed within the lumen 112 of the elongate shaft 110, the first axial lumen of the first portion 172 of the release mechanism 170, and the second axial lumen of the second portion 174 of the release mechanism 170.

The method may include unlocking a retention mechanism between the proximal release wire 120 and the elongate shaft 110 to uncouple the proximal release wire 120 from the elongate shaft 110. The method may further include translating the proximal release wire 120 proximally away from the proximal end 114 of the elongate shaft 110 while the elongate shaft 110 is maintained in a fixed position with respect to the treatment site to translate the proximal release wire 120 and/or the distal release wire 122 relative to the elongate shaft 110 and/or the release mechanism 170 to shift the distal release wire 122 from an interlocked position to a released position, thereby releasing the medical device 130 from the elongate shaft 110.

The method may also include proximal withdrawal of the elongate shaft 110 and/or the microcatheter 190 from the treatment site. For example, in some embodiments, the elongate shaft 110 may be withdrawn proximally through the lumen 192 of the microcatheter 190 and removed, and the microcatheter 190 may then be withdrawn and/or removed from the patient's anatomy. In some embodiments, the elongate shaft 110 may be withdrawn proximally far enough for the distal end 116 of the elongate shaft 110 and/or the first portion 172 of the release mechanism 170 to be positioned within the distal end and/or the lumen 192 of the microcatheter 190. The elongate shaft 110 and the microcatheter 190 may then be withdrawn together from the patient's anatomy.

In some embodiments, the elongate shaft 110 may be removed through the lumen 192 of the microcatheter 190, and the microcatheter 190 may be left and/or held in place within the patient's anatomy. If needed, a second elongate shaft and associated second medical device may then be inserted into the proximal end of the lumen 192 of the microcatheter 190 and advanced to the treatment site for deployment. Additional repetitions of the device(s) described herein, as well as the described method steps, may be used as needed or desired for a particular procedure.

Figure 10:
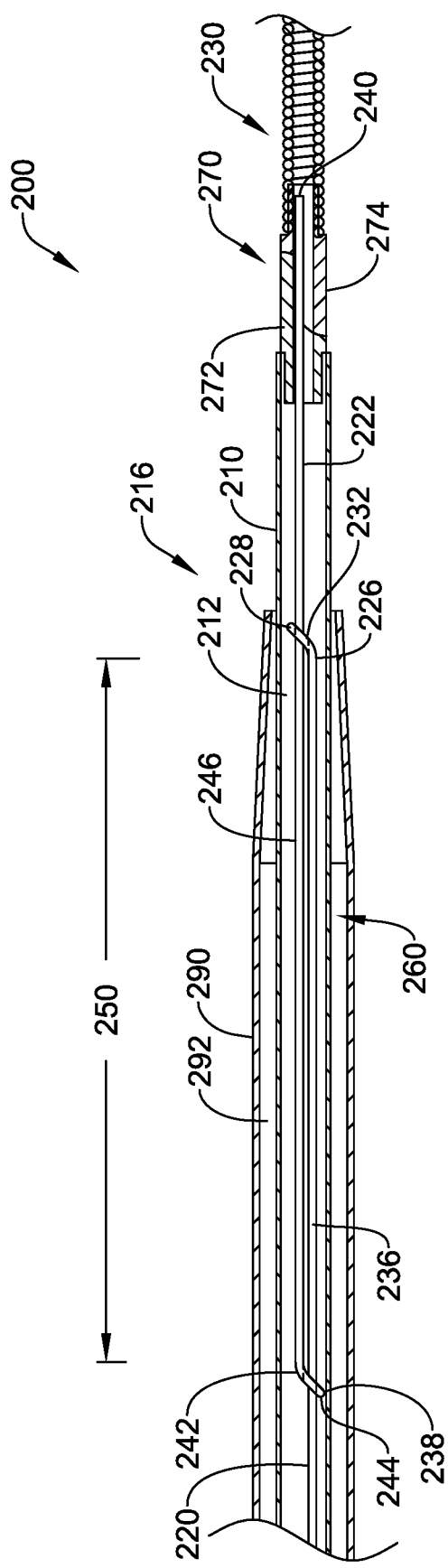
FIG. 10 illustrates a partial cut-away view of another example medical device system.

FIG. 10 illustrates aspects of another example medical device system 200. FIG. 10 is a partial cross-sectional view of the distal end region 216 of the elongate shaft 210. The medical device system 200 may include an elongate shaft 210 having a lumen 212 extending from a proximal end (not explicitly shown) of the elongate shaft 210 to a distal end region 216 of the elongate shaft 210. The elongate shaft 210 may be similar in form and function to the elongate shaft 110 described herein. In some embodiments, the elongate shaft 210 may be a catheter, a hypotube, or other similar tubular structure. In some embodiments, at least a portion of the elongate shaft 210 may include micromachining, a plurality of cuts or weakened areas, some degree of material removal, etc. to provide increased flexibility along a length of the elongate shaft 210 for navigating tortuous vasculature. Some suitable but non-limiting materials for the elongate shaft 210, for example metallic materials, polymer materials, composite materials, etc., are described below.

The medical device system 200 may include a proximal release wire (or a delivery system pull wire) 220 and a distal release wire (or a coupler pull wire) 222 slidably disposed within the lumen 212 of the elongate shaft 210. A medical device 230 may be disposed proximate the distal end of the elongate shaft 210. The medical device 230 may be similar in form and function to the medical device 130 described herein. The proximal and distal release wires 220, 222 may be axially slidable between an interlocked position and a released position relative to the medical device 230, as will be described in more detail herein. The proximal and distal release wires 220, 222 may be configured to releasably attach the medical device 230 to the distal end 216 of the elongate shaft 210. In some embodiments, the proximal and/or distal release wires 220, 222 may be alternately and/or interchangeably referred to as a pull wire, an actuation wire, and/or a locking wire. The proximal and/or distal release wires 220, 222 may generally be a solid wire or shaft, but may also be tubular in some embodiments. Some suitable but non-limiting materials for the proximal and/or distal release wires 220, 222, for example metallic materials, polymer materials, composite materials, etc., are described below.

In some embodiments, the medical device system 200 may include a microcatheter 290 sized and configured to deliver the medical device to a treatment site in a delivery configuration. The elongate shaft 210 and the medical device 230 may be slidably disposed within a lumen 292 of the microcatheter 290. In some embodiments, the microcatheter 290 may facilitate percutaneous delivery of the medical device to the treatment site. Some suitable but non-limiting materials for the microcatheter 290, for example metallic materials, polymer materials, composite materials, etc., are described below.

The proximal release wire 220 extends distally from a proximal end (not explicitly shown) configured to remain outside of the body to a distal end 226. In some cases, the distal end 226 of the proximal release wire 220 may be positioned proximal to the medical device 230. The distal end 226 may be coiled to form a distal stopper including a loop 228 defining a lumen 232 extending therethrough. In some cases, a free end of the loop 228 may be connected or secured to the proximal release wire 220 or a portion of the loop 228. In other embodiments, the free end of the loop 228 may be spaced from and/or unsecured to the proximal release wire 220 and/or other portions of the loop 228. The outer diameter of the loop 228 may be larger than an outer diameter of the wire forming the loop 228. While not explicitly shown, the proximal release wire 220 may include a proximal stopper which may limit proximal movement of the distal release wire 222 and/or facilitate loading of the system.

The distal release wire 222 extends distally from a proximal end 238 to a distal end 240. The distal end 240 of the distal release wire 222 may be slidably coupled with a release mechanism 270 as will be described in more detail herein. The proximal end 238 may be positioned proximal to the distal end 226 of the proximal release wire 220. For example, a proximal end region of the distal release wire 222 may overlap a portion of a length of the distal end region of the proximal release wire 220. The proximal end 238 may be coiled to form a loop 242 defining a lumen 244 extending therethrough. In some cases, a free end of the loop 242 may be connected or secured to the distal release wire 222 or a portion of the loop 242. In other embodiments, the free end of the loop 242 may be spaced from and/or unsecured to the distal release wire 222 and/or other portions of the loop 242. The outer diameter of the loop 242 may be larger than an outer diameter of the wire forming the loop 242. It is contemplated that the loops 228, 242 may be sized such that proximal retraction of the proximal release wire 220 will cause the distal loop 228 of the proximal release wire 220 to mechanically interface with the proximal loop 242 of the distal release wire 222.

In some embodiments the loops 228, 242 may be formed by using metal pull wires and forming an end thereof into a loop or coil. It is contemplated that some illustrative metals may include stainless steel, nitinol, and other as described in more detail below. If nitinol is used, heat setting can be utilized to form a coiled section to the specific geometry desired.

The distal loop 228 of the proximal release wire 220 may be slidably disposed over or generally surround a linear portion 246 of the distal release wire 222 distal to the proximal loop 242 of the distal release wire 222 such that the linear portion 246 of the distal release wire 222 is slidably disposed within the lumen 232 of the distal loop 228. The proximal loop 242 of the distal release wire 222 may be slidably disposed over or generally surround a linear portion 236 of the proximal release wire 220 proximal to the distal loop 228 of the proximal release wire such that the linear portion 236 of the proximal release wire 220 is slidably disposed within the lumen 244 of proximal loop 242. This arrangement may form a slip joint 260. In some cases, the configuration of the slip joint 260 may reduce the risk of the slip joint 260 binding during delivery. The distal loop 228 of the proximal release wire 220 may be spaced a distance from the proximal loop 242 of the distal release wire 222 to provide a slip joint clearance 250. The slip joint clearance 250 may be the longitudinal distance the proximal release wire 220 can move (in at least the proximal direction) without simultaneously moving the distal release wire 222. This may allow the proximal release wire 220 and the distal release wire 222 to be slidably coupled to one another over a limited axial distance (e.g., along a longitudinal axis of the system 200). It is contemplated that the proximal release wire 220 and the distal release wire 222 may each move independently relative to one another over the limited axial distance. The slip joint clearance 250 may determine how far the proximal release wire 220 and/or distal release wire 222 can slide independently before engaging the other component 220, 222 and moving it as well. The slip joint clearance 250 can be modified by changing a position of the proximal release wire 220 relative to the distal release wire 222 and securing the proximal release wire 220 in said position relative to the elongate shaft 210. In some cases, the slip joint clearance 250 may each have a length in the range of about 0.25 centimeters (cm) to about 3 cm, about 0.5 cm to about 2 cm, about 0.75 cm to about 1.25 cm, or about 1 cm. It is contemplated that the slip joint clearance 250 may have lengths less than 0.25 cm or greater than 3 cm depending on the application.

The sliding arrangement of the proximal release wire 220 and the distal release wire 222 may help mitigate premature detachment of the medical device 230. For example, when the delivery system 200 (and the medical device 230) is proximally retracted (and at other times during use), the elongate shaft 210 can experience tensile loading. In other words, the distal portion of the elongate shaft 210 may stretch which may cause the retention wire to prematurely detach from the medical device 230. The proximal end of the proximal release wire 220 (or a region adjacent thereto) may be coupled to the proximal end of the elongate shaft 210 (or a region adjacent thereto) to limit or prevent movement of the proximal release wire 220 relative to the elongate shaft. However, this may cause the proximal release wire 220 to stretch with the elongate shaft 210. The sliding arrangement of the proximal release wire 220 and the distal release wire 222 may allow the proximal release wire 220 to move proximally (e.g., stretch) as the distal portion of the elongate shaft 210 stretches without exerting a proximal force on the distal release wire 222. For example, the proximal release wire 220 and distal release wire 222 may be arranged such that the distal loop 228 of the proximal release wire 220 may be spaced a distance from the proximal loop 242 of the distal release wire 222. This may allow the proximal release wire 220 to move proximally the entire length of the slip joint clearance 250 before the proximal force is applied to the distal release wire 222. Once the distal loop 228 of the proximal release wire 220 engages the proximal loop 242 of the distal release wire 222, the distal release wire 222 moves proximally with the proximal release wire 220, as will be described in more detail herein.

In use, the microcatheter 290 of the medical device system 200 may be inserted into a patient's anatomy and a distal end of the microcatheter 290 may be guided and/or advanced to a location adjacent a treatment site. The medical device 230 disposed at and/or proximate the distal end 216 of the elongate shaft 210 may be inserted into a proximal end of the lumen 292, disposed within the microcatheter 290, and advanced through and/or with the microcatheter 290 to the treatment site. In some embodiments, the medical device 230 may be disposed within the lumen 292 of the microcatheter 290 proximate the distal end of the microcatheter 290. In some embodiments, the medical device 230 may be disposed within the lumen 292 of the microcatheter 290 proximate the distal end of the microcatheter 290 prior to use and/or prior to inserting the microcatheter 290 into the patient's anatomy. Deployment and/or release of the medical device 230 may be performed selectively depending upon the type of medical device and/or the desired treatment process or method. When ready to deploy the medical device 230, the elongate shaft 210 may be advanced and/or translated distally relative to the microcatheter 290 until the medical device 230 is exposed and/or disposed distal of the microcatheter 290. Alternatively, the microcatheter 290 may be withdrawn relative to the elongate shaft 210 until the medical device 230 is exposed and/or disposed distal of the microcatheter 290. For clarity, the microcatheter 290 is shown in a proximally retracted configuration. However, during navigation through the body, the microcatheter may be disposed over the medical device 230.

A release mechanism 270 may releasably attach the medical device 230 to the distal end 216 of the elongate shaft 210. In some embodiments, the elongate shaft 210 may include a first portion 272 of the release mechanism 270 fixedly attached to the distal end 216 of the elongate shaft 210 and the medical device 230 may include a second portion 274 of the release mechanism 270 fixedly attached to a proximal end of the medical device 230. A distal end 240 of the distal release wire 222 may slidably engage with the first portion 272 of the release mechanism 270 and the second portion 274 of the release mechanism 270 in the interlocked position, as seen in FIG. 10. The distal release wire 222 interlocks the first portion 272 of the release mechanism 270 with the second portion 274 of the release mechanism 270 when the proximal release wire 220 and the distal release wire 222 are in the delivery configuration, as shown in FIG. 10.

As the delivery system 200 is distally advanced to the treatment location, the elongate shaft 210 may start to stretch. In some instances, the proximal release wire 220 may be coupled to the elongate shaft 210 to prevent longitudinal movement of the proximal release wire 220 relative to the elongate shaft 210 during delivery. This may cause the proximal release wire 220 to stretch with the elongate shaft 210. While not explicitly shown, as the proximal release wire 220 is shifted in the proximal direction the distal release wire 222 may remain longitudinally fixed, thus reducing the distance of the slip joint clearance 250.

When detachment of the medical device 230 is desired, the user may uncouple the elongate shaft 210 and the proximal release wire 220, if so attached, to allow for proximal retraction of the proximal release wire 220. The proximal end (not explicitly shown) of the proximal release wire 220 may be proximally actuated over a first distance until a length of the clearance 250 of the slip joint 260 has been used up. It is contemplated that the length of the clearance 250 may be variable depending on the degree of stretching of the elongate shaft 210 and/or the original configuration of the distal loop 228 relative to the proximal loop 242. Once the distal loop 228 of the proximal release wire 220 engages the proximal loop 242 of the distal release wire 222 further proximal movement of the proximal release wire 220 over a second distance (e.g., beyond the predetermined distance of the clearance or greater than the first distance) results in proximal actuation of the distal release wire 222 with the proximal release wire 220. In some cases, the proximal loop 242 of the distal release wire 222 may have an interference fit with (or otherwise frictionally or physically engage) the inner wall of the elongate shaft 210. This may secure the distal release wire 222 until force is intentionally applied by the user to the proximal release wire 220. Such an arrangement may help reduce passive migration of the distal release wire 222.

It is contemplated that the release mechanism 270 may remain in an interlocked configuration until the distal release wire 222 has been proximally actuated by a length equal to or greater than the length of the release mechanism 270. For example, proximal actuation of the distal release wire 222 by a length less than a length of the release mechanism 270 may not be sufficient to release the medical device 230. In at least some embodiments, the distal release wire 222 may be slidably disposed within the lumen 212 extending through the elongate shaft 210, a first axial lumen extending through the first portion 272 of the release mechanism 270, and a second axial lumen extending through the second portion 274 of the release mechanism 270. It is contemplated that the release of the medical device 230 may be reversed at any axial location of the distal release wire 222 between the interlocked configuration and a fully released configuration. The first axial lumen of the first portion 272 and the second axial lumen of the second portion 274 may be substantially coaxial with the central longitudinal axis and/or the distal release wire 222 when the medical device 230 is releasably attached to the distal end 216 of the elongate shaft 210. Some suitable but non-limiting materials for the release mechanism 270, the first portion 272, and the second portion 274, for example metallic materials, polymer materials, composite materials, etc., are described below. In use, a method of delivering the medical device 230 to a treatment site (e.g., a vein, an artery, etc.) may be similar to the method described with respect to the medical device 130.

Figure 11:
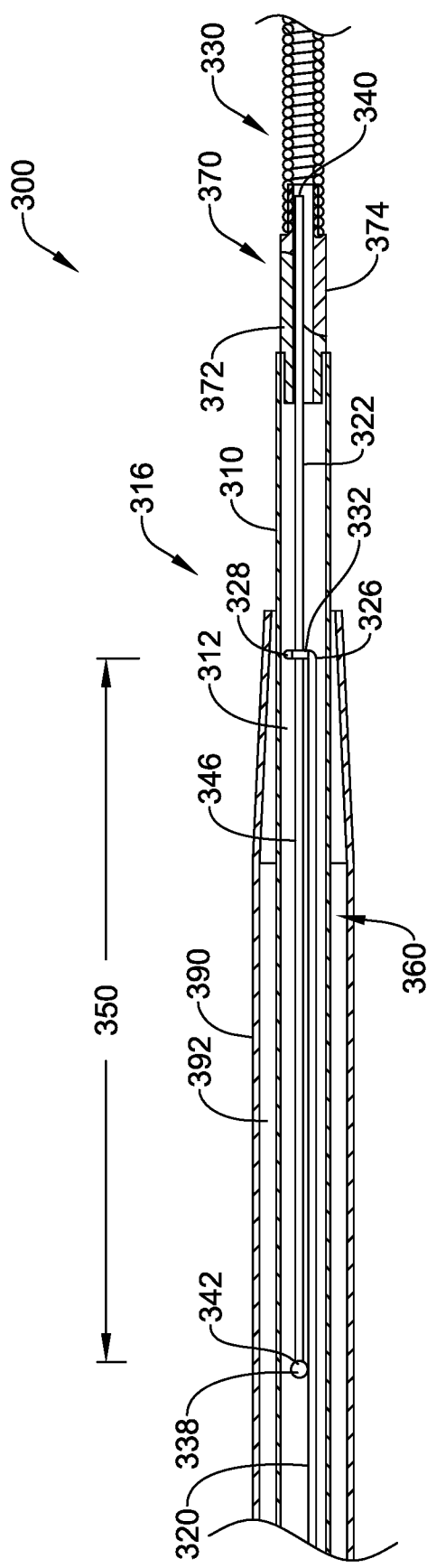
FIG. 11 illustrates a partial cut-away view of another example medical device system.

FIG. 11 illustrates aspects of another example medical device system 300. FIG. 11 is a partial cross-sectional view of the distal end region 316 of the elongate shaft 310. The medical device system 300 may include an elongate shaft 310 having a lumen 312 extending from a proximal end (not explicitly shown) of the elongate shaft 310 to a distal end region 316 of the elongate shaft 310. The elongate shaft 310 may be similar in form and function to the elongate shaft 110 described herein. In some embodiments, the elongate shaft 310 may be a catheter, a hypotube, or other similar tubular structure. In some embodiments, at least a portion of the elongate shaft 310 may include micromachining, a plurality of cuts or weakened areas, some degree of material removal, etc. to provide increased flexibility along a length of the elongate shaft 310 for navigating tortuous vasculature. Some suitable but non-limiting materials for the elongate shaft 310, for example metallic materials, polymer materials, composite materials, etc., are described below.

The medical device system 300 may include a proximal release wire (or a delivery system pull wire) 320 and a distal release wire (or a coupler pull wire) 322 slidably disposed within the lumen 312 of the elongate shaft 310. A medical device 330 may be disposed proximate the distal end of the elongate shaft 310. The medical device 330 may be similar in form and function to the medical device 130 described herein. The proximal and distal release wires 320, 322 may be axially slidable between an interlocked position and a released position relative to the medical device 330, as will be described in more detail herein. The proximal and distal release wires 320, 322 may be configured to releasably attach the medical device 330 to the distal end 316 of the elongate shaft 310. In some embodiments, the proximal and/or distal release wires 320, 322 may be alternately and/or interchangeably referred to as a pull wire, an actuation wire, and/or a locking wire. The proximal and/or distal release wires 320, 322 may generally be a solid wire or shaft, but may also be tubular in some embodiments. Some suitable but non-limiting materials for the proximal and/or distal release wires 320, 322, for example metallic materials, polymer materials, composite materials, etc., are described below.

In some embodiments, the medical device system 300 may include a microcatheter 390 sized and configured to deliver the medical device to a treatment site in a delivery configuration. The elongate shaft 310 and the medical device 330 may be slidably disposed within a lumen 392 of the microcatheter 390. In some embodiments, the microcatheter 390 may facilitate percutaneous delivery of the medical device to the treatment site. Some suitable but non-limiting materials for the microcatheter 390, for example metallic materials, polymer materials, composite materials, etc., are described below.

The proximal release wire 320 extends distally from a proximal end (not explicitly shown) configured to remain outside of the body to a distal end 326. In some cases, the distal end 326 of the proximal release wire 320 may be positioned proximal to the medical device 330. The distal end 326 may include a distal stopper coiled to form a loop 328 defining a lumen 332 extending therethrough. In some cases, a free end of the loop 328 may be connected or secured to the proximal release wire 320 or a portion of the loop 328. In other embodiments, the free end of the loop 328 may be spaced from and/or unsecured to the proximal release wire 320 and/or other portions of the loop 328. In some embodiments the loop 328 may be formed by using metal pull wires and forming an end thereof into a loop or coil. It is contemplated that some illustrative metals may include stainless steel, nitinol, and other as described in more detail below. If nitinol is used, heat setting can be utilized to form a coiled section to the specific geometry desired. The outer diameter of the loop 328 may be larger than an outer diameter of the wire forming the loop 328. While not explicitly shown, the proximal release wire 320 may include a proximal stopper which may limit proximal movement of the distal release wire 322 and/or facilitate loading of the system.

The distal release wire 322 extends distally from a proximal end 338 to a distal end 340. The distal end 340 of the distal release wire 322 may be slidably coupled with a release mechanism 370 as will be described in more detail herein. The proximal end 338 may be positioned proximal to the distal end 326 of the proximal release wire 320. For example, a proximal end region of the distal release wire 322 may overlap a portion of a length of the distal end region of the proximal release wire 320. The proximal end 338 may include a ball or sphere 342 having a diameter (or outer dimension) that is greater than a diameter of the lumen 332 of the loop 328 of the proximal release wire 320, such that the ball 342 cannot pass through the lumen 332. The ball 342 may be formed as a single monolithic structure with the distal release wire 322. In other embodiments, the ball 342 may be separately formed and subsequently attached (e.g., soldered, brazed, welded, adhered, etc.) to the distal release wire 322. While the ball 342 adjacent the proximal end 338 is shown and described as having a generally spherical shape, it is contemplated that other three-dimensional shapes, such as, but not limited to, discs, ellipsoid, ovoid, polygonal, cubic, conical, pyramidal, cylindrical, eccentric shapes, j-hooks etc., may be used as desired.

The distal loop 328 of the proximal release wire 320 may be slidably disposed over or generally surround a linear portion 346 of the distal release wire 322 distal to the ball 342 of the distal release wire 322 such that the linear portion 346 of the distal release wire 322 is slidably disposed within the lumen 332 of the distal loop 328. This arrangement may form a slip joint 360. In some cases, the configuration of the slip joint 360 may reduce the risk of the slip joint 360 binding during delivery. The distal loop 328 of the proximal release wire 320 may be spaced a distance from the ball 342 of the distal release wire 322 to provide a slip joint clearance 350. The slip joint clearance 350 may be the longitudinal distance the proximal release wire 320 can move (in at least the proximal direction) without simultaneously moving the distal release wire 322. This may allow the proximal release wire 320 and the distal release wire 322 to be slidably coupled to one another over a limited axial distance (e.g., along a longitudinal axis of the system 300). It is contemplated that the proximal release wire 320 and the distal release wire 322 may each move independently relative to one another over the limited axial distance. The slip joint clearance 350 may determine how far the proximal release wire 320 and/or distal release wire 322 can slide independently before engaging the other component 320, 322 and moving it as well. The slip joint clearance 350 can be modified by changing a position of the proximal release wire 320 relative to the distal release wire 322 and securing the proximal release wire 320 in said position relative to the elongate shaft 310. In some cases, the slip joint clearance 350 may each have a length in the range of about 0.25 centimeters (cm) to about 3 cm, about 0.5 cm to about 2 cm, about 0.75 cm to about 1.25 cm, or about 1 cm. It is contemplated that the slip joint clearance 350 may have lengths less than 0.25 cm or greater than 3 cm depending on the application.

The sliding arrangement of the proximal release wire 320 and the distal release wire 322 may help mitigate premature detachment of the medical device 330. For example, when the delivery system 300 (and the medical device 330) is proximally retracted (and at other times during use), the elongate shaft 310 can experience tensile loading. In other words, the distal portion of the elongate shaft 310 may stretch which may cause the retention wire to prematurely detach from the medical device 330. The proximal end of the proximal release wire 320 (or a region adjacent thereto) may be coupled to the proximal end of the elongate shaft 310 (or a region adjacent thereto) to limit or prevent movement of the proximal release wire 320 relative to the elongate shaft. However, this may cause the proximal release wire 320 to stretch with the elongate shaft 310. The sliding arrangement of the proximal release wire 320 and the distal release wire 322 may allow the proximal release wire 320 to move proximally (e.g., stretch) as the distal portion of the elongate shaft 310 stretches without exerting a proximal force on the distal release wire 322. For example, the proximal release wire 320 and distal release wire 322 may be arranged such that the distal loop 328 of the proximal release wire 320 may be spaced a distance from the ball 342 of the distal release wire 322. This may allow the proximal release wire 320 to move proximally the entire length of the slip joint clearance 350 before the proximal force is applied to the distal release wire 322. Once the distal loop 328 of the proximal release wire 320 engages the ball 342 of the distal release wire 322, the distal release wire 322 moves proximally with the proximal release wire 320, as will be described in more detail herein.

In use, the microcatheter 390 of the medical device system 300 may be inserted into a patient's anatomy and a distal end of the microcatheter 390 may be guided and/or advanced to a location adjacent a treatment site. The medical device 330 disposed at and/or proximate the distal end 316 of the elongate shaft 310 may be inserted into a proximal end of the lumen 392, disposed within the microcatheter 390, and advanced through and/or with the microcatheter 390 to the treatment site. In some embodiments, the medical device 330 may be disposed within the lumen 392 of the microcatheter 390 proximate the distal end of the microcatheter 390. In some embodiments, the medical device 330 may be disposed within the lumen 392 of the microcatheter 390 proximate the distal end of the microcatheter 390 prior to use and/or prior to inserting the microcatheter 390 into the patient's anatomy. Deployment and/or release of the medical device 330 may be performed selectively depending upon the type of medical device and/or the desired treatment process or method. When ready to deploy the medical device 330, the elongate shaft 310 may be advanced and/or translated distally relative to the microcatheter 390 until the medical device 330 is exposed and/or disposed distal of the microcatheter 390. Alternatively, the microcatheter 390 may be withdrawn relative to the elongate shaft 310 until the medical device 330 is exposed and/or disposed distal of the microcatheter 390. For clarity, the microcatheter 390 is shown in a proximally retracted configuration. However, during navigation through the body, the microcatheter may be disposed over the medical device 330.

A release mechanism 370 may releasably attach the medical device 330 to the distal end 316 of the elongate shaft 310. In some embodiments, the elongate shaft 310 may include a first portion 372 of the release mechanism 370 fixedly attached to the distal end 316 of the elongate shaft 310 and the medical device 330 may include a second portion 374 of the release mechanism 370 fixedly attached to a proximal end of the medical device 330. A distal end 340 of the distal release wire 322 may slidably engage with the first portion 372 of the release mechanism 370 and the second portion 374 of the release mechanism 370 in the interlocked position, as seen in FIG. 11. The distal release wire 322 interlocks the first portion 372 of the release mechanism 370 with the second portion 374 of the release mechanism 370 when the proximal release wire 320 and the distal release wire 322 are in the delivery configuration, as shown in FIG. 11.

As the delivery system 300 is distally advanced to the treatment location, the elongate shaft 310 may start to stretch. In some instances, the proximal release wire 320 may be coupled to the elongate shaft 310 to prevent longitudinal movement of the proximal release wire 320 relative to the elongate shaft 310 during delivery. This may cause the proximal release wire 320 to stretch with the elongate shaft 310. While not explicitly shown, as the proximal release wire 320 is shifted in the proximal direction the distal release wire 322 may remain longitudinally fixed, thus reducing the distance of the slip joint clearance 350.

When detachment of the medical device 330 is desired, the user may uncouple the elongate shaft 310 and the proximal release wire 320, if so attached, to allow for proximal retraction of the proximal release wire 320. The proximal end (not explicitly shown) of the proximal release wire 320 may be proximally actuated over a first distance until a length of the clearance 350 of the slip joint 360 has been used up. It is contemplated that the length of the clearance 350 may be variable depending on the degree of stretching of the elongate shaft 310 and/or the original configuration of the distal loop 328 relative to the ball 342. Once the distal loop 328 of the proximal release wire 320 engages or physically contacts the ball 342 of the distal release wire 322 further proximal movement of the proximal release wire 320 over a second distance (e.g., beyond the predetermined distance of the clearance or greater than the first distance) results in proximal actuation of the distal release wire 322 with the proximal release wire 320. In some cases, the ball 342 of the distal release wire 322 may have an interference fit with (or otherwise frictionally or physically engage) the inner wall of the elongate shaft 310. This may secure the distal release wire 322 until force is intentionally applied by the user to the proximal release wire 320. Such an arrangement may help reduce passive migration of the distal release wire 322.

It is contemplated that the release mechanism 370 may remain in an interlocked configuration until the distal release wire 322 has been proximally actuated by a length equal to or greater than the length of the release mechanism 370. For example, proximal actuation of the distal release wire 322 by a length less than a length of the release mechanism 370 may not be sufficient to release the medical device 330. In at least some embodiments, the distal release wire 322 may be slidably disposed within the lumen 312 extending through the elongate shaft 310, a first axial lumen extending through the first portion 372 of the release mechanism 370, and a second axial lumen extending through the second portion 374 of the release mechanism 370. It is contemplated that the release of the medical device 330 may be reversed at any axial location of the distal release wire 322 between the interlocked configuration and a fully released configuration. The first axial lumen of the first portion 372 and the second axial lumen of the second portion 374 may be substantially coaxial with the central longitudinal axis and/or the distal release wire 322 when the medical device 330 is releasably attached to the distal end 316 of the elongate shaft 310. Some suitable but non-limiting materials for the release mechanism 370, the first portion 372, and the second portion 374, for example metallic materials, polymer materials, composite materials, etc., are described below. In use, a method of delivering the medical device 330 to a treatment site (e.g., a vein, an artery, etc.) may be similar to the method described with respect to the medical device 130.

Figure 12:
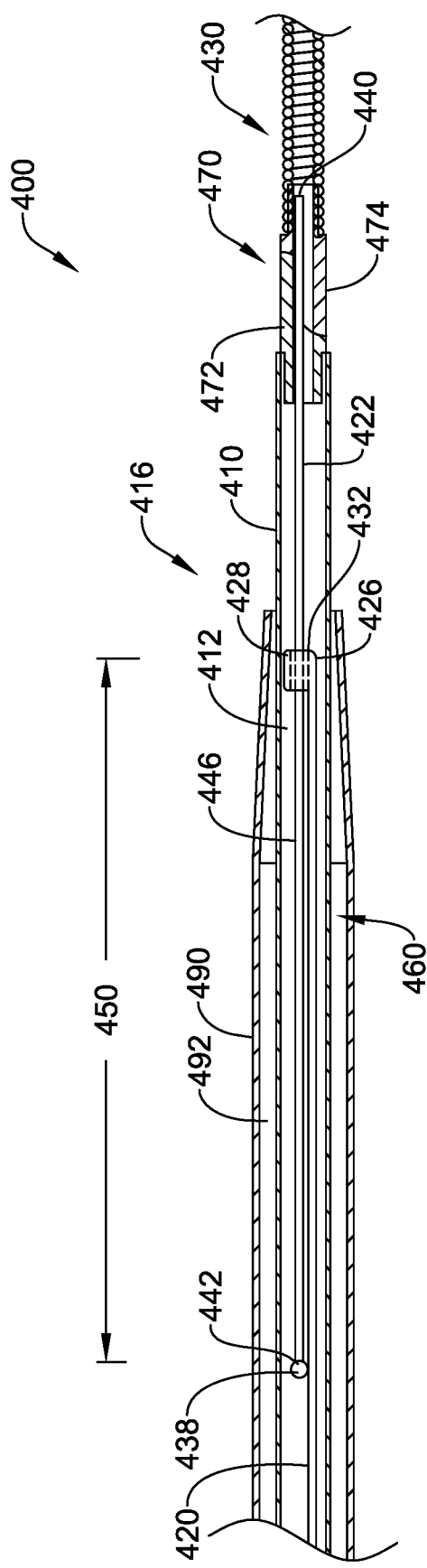
FIG. 12 illustrates a partial cut-away view of another example medical device system.

FIG. 12 illustrates aspects of another example medical device system 400. FIG. 12 is a partial cross-sectional view of the distal end region 416 of the elongate shaft 410. The medical device system 400 may include an elongate shaft 410 having a lumen 412 extending from a proximal end (not explicitly shown) of the elongate shaft 410 to a distal end region 416 of the elongate shaft 410. The elongate shaft 410 may be similar in form and function to the elongate shaft 110 described herein. In some embodiments, the elongate shaft 410 may be a catheter, a hypotube, or other similar tubular structure. In some embodiments, at least a portion of the elongate shaft 410 may include micromachining, a plurality of cuts or weakened areas, some degree of material removal, etc. to provide increased flexibility along a length of the elongate shaft 410 for navigating tortuous vasculature. Some suitable but non-limiting materials for the elongate shaft 410, for example metallic materials, polymer materials, composite materials, etc., are described below.

The medical device system 400 may include a proximal release wire (or a delivery system pull wire) 420 and a distal release wire (or a coupler pull wire) 422 slidably disposed within the lumen 412 of the elongate shaft 410. A medical device 430 may be disposed proximate the distal end of the elongate shaft 410. The medical device 430 may be similar in form and function to the medical device 130 described herein. The proximal and distal release wires 420, 422 may be axially slidable between an interlocked position and a released position relative to the medical device 430, as will be described in more detail herein. The proximal and distal release wires 420, 422 may be configured to releasably attach the medical device 430 to the distal end 416 of the elongate shaft 410. In some embodiments, the proximal and/or distal release wires 420, 422 may be alternately and/or interchangeably referred to as a pull wire, an actuation wire, and/or a locking wire. The proximal and/or distal release wires 420, 422 may generally be a solid wire or shaft, but may also be tubular in some embodiments. Some suitable but non-limiting materials for the proximal and/or distal release wires 420, 422, for example metallic materials, polymer materials, composite materials, etc., are described below.

In some embodiments, the medical device system 400 may include a microcatheter 490 sized and configured to deliver the medical device to a treatment site in a delivery configuration. The elongate shaft 410 and the medical device 430 may be slidably disposed within a lumen 492 of the microcatheter 490. In some embodiments, the microcatheter 490 may facilitate percutaneous delivery of the medical device to the treatment site. Some suitable but non-limiting materials for the microcatheter 490, for example metallic materials, polymer materials, composite materials, etc., are described below.

The proximal release wire 420 extends distally from a proximal end (not explicitly shown) configured to remain outside of the body to a distal end 426. In some cases, the distal end 426 of the proximal release wire 420 may be positioned proximal to the medical device 430. The distal end 426 may include a generally cylindrical collar or sleeve 428 defining a lumen 432 extending therethrough. The collar 428 may be formed as a single monolithic structure with the proximal release wire 420. In other embodiments, the collar 428 may be separately formed and subsequently attached (e.g., soldered, brazed, welded, adhered, etc.) to the proximal release wire 420. The collar 428 may have an outer diameter that is greater than an outer diameter of the remainder of the proximal release wire 420. While not explicitly shown, the proximal release wire 420 may include a proximal stopper which may limit proximal movement of the distal release wire 422 and/or facilitate loading of the system.

The distal release wire 422 extends distally from a proximal end 438 to a distal end 440. The distal end 440 of the distal release wire 422 may be slidably coupled with a release mechanism 470 as will be described in more detail herein. The proximal end 438 may be positioned proximal to the distal end 426 of the proximal release wire 420. For example, a proximal end region of the distal release wire 422 may overlap a portion of a length of the distal end region of the proximal release wire 420. The proximal end 438 may include a ball or sphere 442 having a diameter (or outer dimension) that is greater than a diameter of the lumen 432 of the collar 428 of the proximal release wire 420, such that the ball 442 cannot pass through the lumen 432. The ball 442 may be formed as a single monolithic structure with the distal release wire 422. In other embodiments, the ball 442 may be separately formed and subsequently attached (e.g., soldered, brazed, welded, adhered, etc.) to the proximal release wire 422. While the ball 442 adjacent the proximal end 438 is shown and described as having a generally spherical shape, it is contemplated that other three-dimensional shapes, such as, but not limited to, discs, ellipsoid, ovoid, polygonal, cubic, conical, pyramidal, cylindrical, eccentric shapes, j-hooks etc., may be used as desired.

The collar 428 of the proximal release wire 420 may be slidably disposed over or generally surround a linear portion 446 of the distal release wire 422 distal to the ball 442 of the distal release wire 422 such that the linear portion 446 of the distal release wire 422 is slidably disposed within the lumen 432 of the collar 428. This arrangement may form a slip joint 460. In some cases, the configuration of the slip joint 460 may reduce the risk of the slip joint 460 binding during delivery. The collar 428 of the proximal release wire 420 may be spaced a distance from the ball 442 of the distal release wire 422 to provide a slip joint clearance 450. The slip joint clearance 450 may be the longitudinal distance the proximal release wire 420 can move (in at least the proximal direction) without simultaneously moving the distal release wire 422. This may allow the proximal release wire 420 and the distal release wire 422 to be slidably coupled to one another over a limited axial distance (e.g., along a longitudinal axis of the system 400). It is contemplated that the proximal release wire 420 and the distal release wire 422 may each move independently relative to one another over the limited axial distance. The slip joint clearance 450 may determine how far the proximal release wire 420 and/or distal release wire 422 can slide independently before engaging the other component 420, 422 and moving it as well. The slip joint clearance 450 can be modified by changing a position of the proximal release wire 420 relative to the distal release wire 422 and securing the proximal release wire 420 in said position relative to the elongate shaft 410. In some cases, the slip joint clearance 450 may each have a length in the range of about 0.25 centimeters (cm) to about 3 cm, about 0.5 cm to about 2 cm, about 0.75 cm to about 1.25 cm, or about 1 cm. It is contemplated that the slip joint clearance 450 may have lengths less than 0.25 cm or greater than 3 cm depending on the application.

The sliding arrangement of the proximal release wire 420 and the distal release wire 422 may help mitigate premature detachment of the medical device 430. For example, when the delivery system 400 (and the medical device 430) is proximally retracted (and at other times during use), the elongate shaft 410 can experience tensile loading. In other words, the distal portion of the elongate shaft 410 may stretch which may cause the retention wire to prematurely detach from the medical device 430. The proximal end of the proximal release wire 420 (or a region adjacent thereto) may be coupled to the proximal end of the elongate shaft 410 (or a region adjacent thereto) to limit or prevent movement of the proximal release wire 420 relative to the elongate shaft. However, this may cause the proximal release wire 420 to stretch with the elongate shaft 410. The sliding arrangement of the proximal release wire 420 and the distal release wire 422 may allow the proximal release wire 420 to move proximally (e.g., stretch) as the distal portion of the elongate shaft 410 stretches without exerting a proximal force on the distal release wire 422. For example, the proximal release wire 420 and distal release wire 422 may be arranged such that the collar 428 of the proximal release wire 420 may be spaced a distance from the ball 442 of the distal release wire 422. This may allow the proximal release wire 420 to move proximally the entire length of the slip joint clearance 450 before the proximal force is applied to the distal release wire 422. Once the collar 428 of the proximal release wire 420 engages or contacts the ball 442 of the distal release wire 422, the distal release wire 422 moves proximally with the proximal release wire 420, as will be described in more detail herein.

In use, the microcatheter 490 of the medical device system 400 may be inserted into a patient's anatomy and a distal end of the microcatheter 490 may be guided and/or advanced to a location adjacent a treatment site. The medical device 430 disposed at and/or proximate the distal end 416 of the elongate shaft 410 may be inserted into a proximal end of the lumen 492, disposed within the microcatheter 490, and advanced through and/or with the microcatheter 490 to the treatment site. In some embodiments, the medical device 430 may be disposed within the lumen 492 of the microcatheter 490 proximate the distal end of the microcatheter 490. In some embodiments, the medical device 430 may be disposed within the lumen 492 of the microcatheter 490 proximate the distal end of the microcatheter 490 prior to use and/or prior to inserting the microcatheter 490 into the patient's anatomy. Deployment and/or release of the medical device 430 may be performed selectively depending upon the type of medical device and/or the desired treatment process or method. When ready to deploy the medical device 430, the elongate shaft 410 may be advanced and/or translated distally relative to the microcatheter 490 until the medical device 430 is exposed and/or disposed distal of the microcatheter 490. Alternatively, the microcatheter 490 may be withdrawn relative to the elongate shaft 410 until the medical device 430 is exposed and/or disposed distal of the microcatheter 490. For clarity, the microcatheter 490 is shown in a proximally retracted configuration. However, that during navigation through the body, the microcatheter may be disposed over the medical device 430.

A release mechanism 470 may releasably attach the medical device 430 to the distal end 416 of the elongate shaft 410. In some embodiments, the elongate shaft 410 may include a first portion 472 of the release mechanism 470 fixedly attached to the distal end 416 of the elongate shaft 410 and the medical device 430 may include a second portion 474 of the release mechanism 470 fixedly attached to a proximal end of the medical device 430. A distal end 440 of the distal release wire 422 may slidably engage with the first portion 472 of the release mechanism 470 and the second portion 474 of the release mechanism 470 in the interlocked position, as seen in FIG. 12. The distal release wire 422 interlocks the first portion 472 of the release mechanism 470 with the second portion 474 of the release mechanism 470 when the proximal release wire 420 and the distal release wire 422 are in the delivery configuration, as shown in FIG. 12.

As the delivery system 400 is distally advanced to the treatment location, the elongate shaft 410 may start to stretch. In some instances, the proximal release wire 420 may be coupled to the elongate shaft 410 to prevent longitudinal movement of the proximal release wire 420 relative to the elongate shaft 410 during delivery. This may cause the proximal release wire 420 to stretch with the elongate shaft 410. While not explicitly shown, as the proximal release wire 420 is shifted in the proximal direction the distal release wire 422 may remain longitudinally fixed, thus reducing the distance of the slip joint clearance 450.

When detachment of the medical device 430 is desired, the user may uncouple the elongate shaft 410 and the proximal release wire 420, if so attached, to allow for proximal retraction of the proximal release wire 420. The proximal end (not explicitly shown) of the proximal release wire 420 may be proximally actuated over a first distance until a length of the clearance 450 of the slip joint 460 has been used up. It is contemplated that the length of the clearance 450 may be variable depending on the degree of stretching of the elongate shaft 410 and/or the original configuration of the collar 428 relative to the ball 442. Once the collar 428 of the proximal release wire 420 engages or physically contacts the ball 442 of the distal release wire 422 further proximal movement of the proximal release wire 420 over a second distance (e.g., beyond the predetermined distance of the clearance or greater than the first distance) results in proximal actuation of the distal release wire 422 with the proximal release wire 420. In some cases, the ball 442 of the distal release wire 422 may have an interference fit with (or otherwise frictionally or physically engage) the inner wall of the elongate shaft 410. This may secure the distal release wire 422 until force is intentionally applied by the user to the proximal release wire 420. Such an arrangement may help reduce passive migration of the distal release wire 422.

It is contemplated that the release mechanism 470 may remain in an interlocked configuration until the distal release wire 422 has been proximally actuated by a length equal to or greater than the length of the release mechanism 470. For example, proximal actuation of the distal release wire 422 by a length less than a length of the release mechanism 470 may not be sufficient to release the medical device 430. In at least some embodiments, the distal release wire 422 may be slidably disposed within the lumen 412 extending through the elongate shaft 410, a first axial lumen extending through the first portion 472 of the release mechanism 470, and a second axial lumen extending through the second portion 474 of the release mechanism 470. It is contemplated that the release of the medical device 430 may be reversed at any axial location of the distal release wire 422 between the interlocked configuration and a fully released configuration. The first axial lumen of the first portion 472 and the second axial lumen of the second portion 474 may be substantially coaxial with the central longitudinal axis and/or the distal release wire 422 when the medical device 430 is releasably attached to the distal end 416 of the elongate shaft 410. Some suitable but non-limiting materials for the release mechanism 470, the first portion 472, and the second portion 474, for example metallic materials, polymer materials, composite materials, etc., are described below. In use, a method of delivering the medical device 430 to a treatment site (e.g., a vein, an artery, etc.) may be similar to the method described with respect to the medical device 130.

Figure 13:
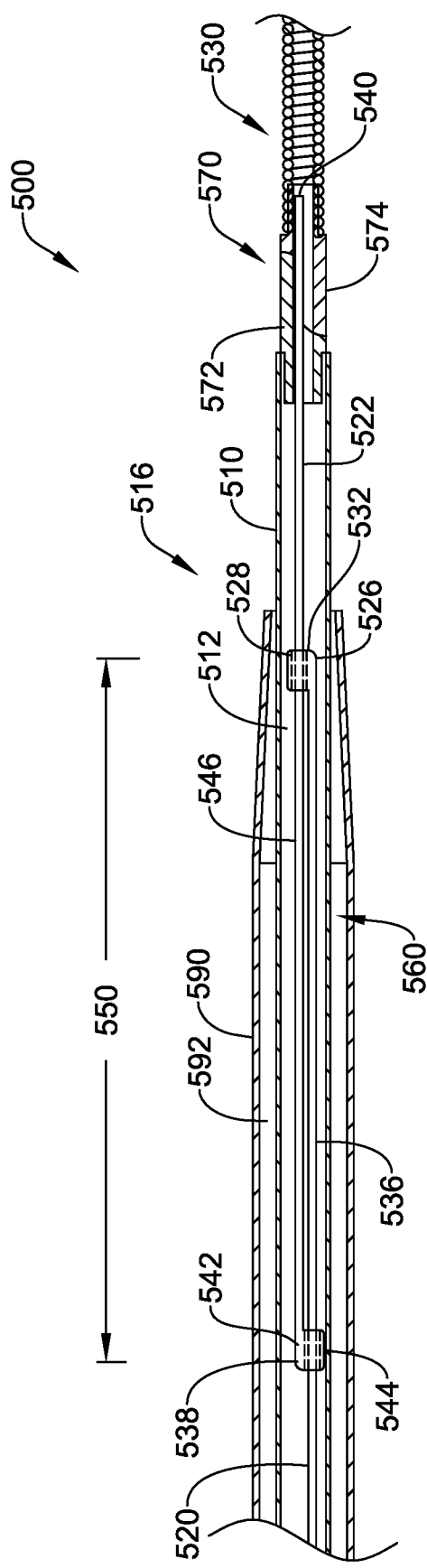
FIG. 13 illustrates a partial cut-away view of another example medical device system.

FIG. 13 illustrates aspects of another example medical device system 500. FIG. 13 is a partial cross-sectional view of the distal end region 516 of the elongate shaft 510. The medical device system 500 may include an elongate shaft 510 having a lumen 512 extending from a proximal end (not explicitly shown) of the elongate shaft 510 to a distal end region 516 of the elongate shaft 510. The elongate shaft 510 may be similar in form and function to the elongate shaft 110 described herein. In some embodiments, the elongate shaft 510 may be a catheter, a hypotube, or other similar tubular structure. In some embodiments, at least a portion of the elongate shaft 510 may include micromachining, a plurality of cuts or weakened areas, some degree of material removal, etc. to provide increased flexibility along a length of the elongate shaft 510 for navigating tortuous vasculature. Some suitable but non-limiting materials for the elongate shaft 510, for example metallic materials, polymer materials, composite materials, etc., are described below.

The medical device system 500 may include a proximal release wire (or a delivery system pull wire) 520 and a distal release wire (or a coupler pull wire) 522 slidably disposed within the lumen 512 of the elongate shaft 510. A medical device 530 may be disposed proximate the distal end of the elongate shaft 510. The medical device 530 may be similar in form and function to the medical device 130 described herein. The proximal and distal release wires 520, 522 may be axially slidable between an interlocked position and a released position relative to the medical device 530, as will be described in more detail herein. The proximal and distal release wires 520, 522 may be configured to releasably attach the medical device 530 to the distal end 516 of the elongate shaft 510. In some embodiments, the proximal and/or distal release wires 520, 522 may be alternately and/or interchangeably referred to as a pull wire, an actuation wire, and/or a locking wire. The proximal and/or distal release wires 520, 522 may generally be a solid wire or shaft, but may also be tubular in some embodiments. Some suitable but non-limiting materials for the proximal and/or distal release wires 520, 522, for example metallic materials, polymer materials, composite materials, etc., are described below.

In some embodiments, the medical device system 500 may include a microcatheter 590 sized and configured to deliver the medical device to a treatment site in a delivery configuration. The elongate shaft 510 and the medical device 530 may be slidably disposed within a lumen 592 of the microcatheter 590. In some embodiments, the microcatheter 590 may facilitate percutaneous delivery of the medical device to the treatment site. Some suitable but non-limiting materials for the microcatheter 590, for example metallic materials, polymer materials, composite materials, etc., are described below.

The proximal release wire 520 extends distally from a proximal end (not explicitly shown) configured to remain outside of the body to a distal end 426. In some cases, the distal end 426 of the proximal release wire 520 may be positioned proximal to the medical device 530. The distal end 426 may include a distal stopper including a generally cylindrical collar or sleeve 528 defining a lumen 532 extending therethrough. The collar 528 may be formed as a single monolithic structure with the proximal release wire 520. In other embodiments, the collar 528 may be separately formed and subsequently attached (e.g., soldered, brazed, welded, adhered, etc.) to the proximal release wire 520. The collar 528 may have an outer diameter that is greater than an outer diameter of the remainder of the proximal release wire 520. While not explicitly shown, the proximal release wire 520 may include a proximal stopper which may limit proximal movement of the distal release wire 522 and/or facilitate loading of the system.

The distal release wire 522 extends distally from a proximal end 538 to a distal end 540. The distal end 540 of the distal release wire 522 may be slidably coupled with a release mechanism 570 as will be described in more detail herein. The proximal end 538 may be positioned proximal to the distal end 426 of the proximal release wire 520. For example, a proximal end region of the distal release wire 522 may overlap a portion of a length of the distal end region of the proximal release wire 520. The proximal end 538 may include a generally cylindrical collar or sleeve 542 defining a lumen 544 extending therethrough. The collar 542 may be formed as a single monolithic structure with the distal release wire 522. In other embodiments, the collar 542 may be separately formed and subsequently attached (e.g., soldered, brazed, welded, adhered, etc.) to the distal release wire 522. The collar 542 may have an outer diameter that is greater than an outer diameter of the remainder of the distal release wire 522.

The collar 528 of the proximal release wire 520 may be slidably disposed over or generally surround a linear portion 546 of the distal release wire 522 distal to the collar 542 of the distal release wire 522 such that the linear portion 546 of the distal release wire 522 is slidably disposed within the lumen 532 of the collar 528. The collar 542 of the distal release wire 522 may be slidably disposed over or generally surround a linear portion 536 of the proximal release wire 520 proximal to the collar 528 of the proximal release wire 520 such that the linear portion 536 of the proximal release wire 520 is slidably disposed within the lumen 544 of the collar 542. This arrangement may form a slip joint 560. In some cases, the configuration of the slip joint 560 may reduce the risk of the slip joint 560 binding during delivery. The collar 528 of the proximal release wire 520 may be spaced a distance from the collar 542 of the distal release wire 522 to provide a slip joint clearance 550. The slip joint clearance 550 may be the longitudinal distance the proximal release wire 520 can move (in at least the proximal direction) without simultaneously moving the distal release wire 522. This may allow the proximal release wire 520 and the distal release wire 522 to be slidably coupled to one another over a limited axial distance (e.g., along a longitudinal axis of the system 500). It is contemplated that the proximal release wire 520 and the distal release wire 522 may each move independently relative to one another over the limited axial distance. The slip joint clearance 550 may determine how far the proximal release wire 520 and/or distal release wire 522 can slide independently before engaging the other component 520, 522 and moving it as well. The slip joint clearance 550 can be modified by changing a position of the proximal release wire 520 relative to the distal release wire 522 and securing the proximal release wire 520 in said position relative to the elongate shaft 510. In some cases, the slip joint clearance 550 may each have a length in the range of about 0.25 centimeters (cm) to about 3 cm, about 0.5 cm to about 2 cm, about 0.75 cm to about 1.25 cm, or about 1 cm. It is contemplated that the slip joint clearance 550 may have lengths less than 0.25 cm or greater than 3 cm depending on the application.

The sliding arrangement of the proximal release wire 520 and the distal release wire 522 may help mitigate premature detachment of the medical device 530. For example, when the delivery system 500 (and the medical device 530) is proximally retracted (and at other times during use), the elongate shaft 510 can experience tensile loading. In other words, the distal portion of the elongate shaft 510 may stretch which may cause the retention wire to prematurely detach from the medical device 530. The proximal end of the proximal release wire 520 (or a region adjacent thereto) may be coupled to the proximal end of the elongate shaft 510 (or a region adjacent thereto) to limit or prevent movement of the proximal release wire 520 relative to the elongate shaft. However, this may cause the proximal release wire 520 to stretch with the elongate shaft 510. The sliding arrangement of the proximal release wire 520 and the distal release wire 522 may allow the proximal release wire 520 to move proximally (e.g., stretch) as the distal portion of the elongate shaft 510 stretches without exerting a proximal force on the distal release wire 522. For example, the proximal release wire 520 and distal release wire 522 may be arranged such that the collar 528 of the proximal release wire 520 may be spaced a distance from the collar 542 of the distal release wire 522. This may allow the proximal release wire 520 to move proximally the entire length of the slip joint clearance 550 before the proximal force is applied to the distal release wire 522. Once the collar 528 of the proximal release wire 520 engages or contacts the collar 542 of the distal release wire 522, the distal release wire 522 moves proximally with the proximal release wire 520, as will be described in more detail herein.

In use, the microcatheter 590 of the medical device system 500 may be inserted into a patient's anatomy and a distal end of the microcatheter 590 may be guided and/or advanced to a location adjacent a treatment site. The medical device 530 disposed at and/or proximate the distal end 516 of the elongate shaft 510 may be inserted into a proximal end of the lumen 592, disposed within the microcatheter 590, and advanced through and/or with the microcatheter 590 to the treatment site. In some embodiments, the medical device 530 may be disposed within the lumen 592 of the microcatheter 590 proximate the distal end of the microcatheter 590. In some embodiments, the medical device 530 may be disposed within the lumen 592 of the microcatheter 590 proximate the distal end of the microcatheter 590 prior to use and/or prior to inserting the microcatheter 590 into the patient's anatomy. Deployment and/or release of the medical device 530 may be performed selectively depending upon the type of medical device and/or the desired treatment process or method. When ready to deploy the medical device 530, the elongate shaft 510 may be advanced and/or translated distally relative to the microcatheter 590 until the medical device 530 is exposed and/or disposed distal of the microcatheter 590. Alternatively, the microcatheter 590 may be withdrawn relative to the elongate shaft 510 until the medical device 530 is exposed and/or disposed distal of the microcatheter 590. For clarity, the microcatheter 590 is shown in a proximally retracted configuration. However, during navigation through the body, the microcatheter may be disposed over the medical device 530.

A release mechanism 570 may releasably attach the medical device 530 to the distal end 516 of the elongate shaft 510. In some embodiments, the elongate shaft 510 may include a first portion 572 of the release mechanism 570 fixedly attached to the distal end 516 of the elongate shaft 510 and the medical device 530 may include a second portion 574 of the release mechanism 570 fixedly attached to a proximal end of the medical device 530. A distal end 540 of the distal release wire 522 may slidably engage with the first portion 572 of the release mechanism 570 and the second portion 574 of the release mechanism 570 in the interlocked position, as seen in FIG. 13. The distal release wire 522 interlocks the first portion 572 of the release mechanism 570 with the second portion 574 of the release mechanism 570 when the proximal release wire 520 and the distal release wire 522 are in the delivery configuration, as shown in FIG. 13.

As the delivery system 500 is distally advanced to the treatment location, the elongate shaft 510 may start to stretch. In some instances, the proximal release wire 520 may be coupled to the elongate shaft 510 to prevent longitudinal movement of the proximal release wire 520 relative to the elongate shaft 510 during delivery. This may cause the proximal release wire 520 to stretch with the elongate shaft 510. While not explicitly shown, as the proximal release wire 520 is shifted in the proximal direction the distal release wire 522 may remain longitudinally fixed, thus reducing the distance of the slip joint clearance 550.

When detachment of the medical device 530 is desired, the user may uncouple the elongate shaft 510 and the proximal release wire 520, if so attached, to allow for proximal retraction of the proximal release wire 520. The proximal end (not explicitly shown) of the proximal release wire 520 may be proximally actuated over a first distance until a length of the clearance 550 of the slip joint 560 has been used up. It is contemplated that the length of the clearance 550 may be variable depending on the degree of stretching of the elongate shaft 510 and/or the original configuration of the collar 528 relative to the collar 542. Once the collar 528 of the proximal release wire 520 engages or physically contacts the collar 542 of the distal release wire 522 further proximal movement of the proximal release wire 520 over a second distance (e.g., beyond the predetermined distance of the clearance or greater than the first distance) results in proximal actuation of the distal release wire 522 with the proximal release wire 520. In some cases, the collar 542 of the distal release wire 522 may have an interference fit with (or otherwise frictionally of physically engage) the inner wall of the elongate shaft 510. This may secure the distal release wire 522 until force is intentionally applied by the user to the proximal release wire 520. Such an arrangement may help reduce passive migration of the distal release wire 522.

It is contemplated that the release mechanism 570 may remain in an interlocked configuration until the distal release wire 522 has been proximally actuated by a length equal to or greater than the length of the release mechanism 570. For example, proximal actuation of the distal release wire 522 by a length less than a length of the release mechanism 570 may not be sufficient to release the medical device 530. In at least some embodiments, the distal release wire 522 may be slidably disposed within the lumen 512 extending through the elongate shaft 510, a first axial lumen extending through the first portion 572 of the release mechanism 570, and a second axial lumen extending through the second portion 574 of the release mechanism 570. It is contemplated that the release of the medical device 530 may be reversed at any axial location of the distal release wire 522 between the interlocked configuration and a fully released configuration. The first axial lumen of the first portion 572 and the second axial lumen of the second portion 574 may be substantially coaxial with the central longitudinal axis and/or the distal release wire 522 when the medical device 530 is releasably attached to the distal end 516 of the elongate shaft 510. Some suitable but non-limiting materials for the release mechanism 570, the first portion 572, and the second portion 574, for example metallic materials, polymer materials, composite materials, etc., are described below. In use, a method of delivering the medical device 530 to a treatment site (e.g., a vein, an artery, etc.) may be similar to the method described with respect to the medical device 130. The materials that can be used for the various components of the medical device systems, the elongate shafts, the release wires, the medical devices, the release mechanisms, the introducer, and/or the microcatheters, etc. (and/or other systems disclosed herein) and the various elements thereof disclosed herein may include those commonly associated with medical devices. For simplicity purposes, the following discussion makes reference to the medical device system, the elongate shaft, the release wires, the medical device, the release mechanism, the introducer, and/or the microcatheter, etc. However, this is not intended to limit the devices and methods described herein, as the discussion may be applied to other elements, members, components, or devices disclosed herein, such as, but not limited to, the medical device system, the elongate shaft, the release wires, the medical device, the release mechanism, the introducer, and/or the microcatheter, etc. and/or elements or components thereof.

In some embodiments, the medical device system, the elongate shaft, the release wires, the medical device, the release mechanism, the introducer, and/or the microcatheter, etc., and/or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system, the elongate shaft, the release wires, the medical device, the release mechanism, the introducer, and/or the microcatheter, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system, the elongate shaft, the release wires, the medical device, the release mechanism, the introducer, and/or the microcatheter, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system, the elongate shaft, the release wires, the medical device, the release mechanism, the introducer, and/or the microcatheter, etc. to achieve the same result.

In some embodiments, a degree of Magnetic Resonance Imaging (MRI) compatibility is imparted the medical device system, the elongate shaft, the release wires, the medical device, the release mechanism, the introducer, and/or the microcatheter, etc. For example, the medical device system, the elongate shaft, the release wires, the medical device, the release mechanism, the introducer, and/or the microcatheter, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system, the elongate shaft, the release wires, the medical device, the release mechanism, the introducer, and/or the microcatheter, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system, the elongate shaft, the release wires, the medical device, the release mechanism, the introducer, and/or the microcatheter, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system, the elongate shaft, the release wires, the medical device, the release mechanism, the introducer, and/or the microcatheter, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system, the elongate shaft, the release wires, the medical device, the release mechanism, the introducer, and/or the microcatheter, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethyl acetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system, the elongate shaft, the release wires, the medical device, the release mechanism, the introducer, and/or the microcatheter, etc. may include and/or be treated with a suitable therapeutic agent. Some examples of suitable therapeutic agents may include anti-thrombogenic agents (such as heparin, heparin derivatives, urokinase, and PPack (dextro phenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed:

1. A medical device system, comprising:
an elongate shaft having a lumen extending from a proximal end of the elongate shaft to a distal end of the elongate shaft;
a proximal release wire extending distally from a proximal end configured to remain outside a body to a distal end including a distal stopper, the distal stopper having a greater cross-sectional dimension than an intermediate region of the proximal release wire and slidably disposed within the lumen of the elongate shaft; and
a distal release wire extending distally from a proximal end including a helical coil to a linear distal end and slidably disposed within the lumen of the elongate shaft, the helical coil of the distal release wire slidably disposed over the intermediate region of the proximal release wire, wherein the distal release wire releasably attaches a medical device to the distal end of the elongate shaft;
wherein proximal movement of the proximal release wire over a first distance moves the proximal release wire independent of the distal release wire and proximal movement of the proximal release wire over a second distance greater than the first distance is configured to move the distal release wire in concert with the proximal release wire to detach the medical device from the distal end of the elongate shaft.

2. The medical device system of claim 1, wherein the first distance is equal to or less than a distance between a proximal end of the distal stopper and a distal end region of the helical coil.

3. The medical device system of claim 2, wherein the proximal end of the distal stopper is configured to engage an inner surface or a distal end of the helical coil of the distal release wire upon proximal actuation of the proximal release wire a distance greater than the first distance.

4. The medical device system of claim 1, wherein at least a portion of the distal release wire extends parallel to the intermediate region of the proximal release wire.

5. A medical device system, comprising:
an elongate shaft having a lumen extending from a proximal end of the elongate shaft to a distal end of the elongate shaft;
a proximal release wire extending distally from a proximal end configured to remain outside a body to a distal end and slidably disposed within the lumen of the elongate shaft;
a distal stopper coupled to the distal end of the proximal release wire;
a proximal stopper coupled to the proximal release wire proximal to the distal stopper; and
a distal release wire extending distally from a proximal end to a linear distal end and slidably disposed within the lumen of the elongate shaft, the proximal end of the distal release wire comprising a plurality of windings slidably coupled over a linear portion of the proximal release wire, wherein the distal release wire releasably attaches a medical device to the distal end of the elongate shaft;

wherein proximal movement of the proximal release wire over a first distance moves the proximal release wire independent of the distal release wire and proximal movement of the proximal release wire over a second distance greater than the first distance is configured to move the distal release wire in concert with the proximal release wire to detach the medical device from the distal end of the elongate shaft.

6. The medical device system of claim 5, wherein the proximal end of the distal release wire is slidably disposed between the proximal stopper and the distal stopper.

7. The medical device system of claim 5, wherein the distal stopper has an outer diameter greater than an inner diameter of the plurality of windings.

* * * * *